(12) United States Patent
Park et al.

(10) Patent No.: US 12,090,210 B2
(45) Date of Patent: Sep. 17, 2024

(54) ANTIBODY-DRUG CONJUGATE COMPRISING MODIFIED ANTIBODY

(71) Applicant: ALTEOGEN, INC., Daejeon (KR)

(72) Inventors: Soon Jae Park, Daejeon (KR);
Hye-Shin Chung, Daejeon (KR);
Sunbae Lee, Daejeon (KR); Minsoo Byun, Daejeon (KR)

(73) Assignee: ALTEOGEN, INC., Daejeon (KR)

( * ) Notice: Subject to any disclaimer, the term of this patent is extended or adjusted under 35 U.S.C. 154(b) by 46 days.

(21) Appl. No.: 17/551,103

(22) Filed: Dec. 14, 2021

(65) Prior Publication Data

US 2022/0105197 A1 Apr. 7, 2022

Related U.S. Application Data

(62) Division of application No. 16/088,804, filed as application No. PCT/KR2017/003508 on Mar. 30, 2017, now Pat. No. 11,235,065.

(30) Foreign Application Priority Data

Apr. 6, 2016 (KR) .................. 10-2016-0042269
Mar. 30, 2017 (KR) .................. 10-2017-0040472

(51) Int. Cl.
*A61K 47/68* (2017.01)
*A61K 47/65* (2017.01)
*A61P 35/00* (2006.01)
*C07K 16/18* (2006.01)
*A61K 45/06* (2006.01)

(52) U.S. Cl.
CPC .......... *A61K 47/6803* (2017.08); *A61K 47/65* (2017.08); *A61P 35/00* (2018.01); *C07K 16/18* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 9,814,782 B2 * | 11/2017 | Park .................. | A61K 38/07 |
| 2014/0303084 A1 | 10/2014 | Thorn et al. | |
| 2016/0102148 A1 | 4/2016 | Park et al. | |
| 2020/0254111 A1 | 8/2020 | Park et al. | |

FOREIGN PATENT DOCUMENTS

| | | | | |
|---|---|---|---|---|
| CN | 101065151 A | 10/2007 | | |
| CN | 102596260 A | 7/2012 | | |
| CN | 102973947 A | 3/2013 | | |
| CN | 104220458 A | 2/2014 | | |
| EP | 2818480 A1 * | 12/2014 | .......... | A61K 31/704 |
| JP | 2015513541 A | 5/2015 | | |
| KR | 102007-0054682 A | 5/2007 | | |
| KR | 102013-0097669 A | 9/2013 | | |
| WO | 2006034488 A3 | 3/2006 | | |
| WO | 2009026274 A1 | 2/2009 | | |

OTHER PUBLICATIONS

Schneider-Merck, Tanja, et al. The journal of immunology 184.1 (2010): 512-520 (Year: 2010).*
Ledermann, J. A., Silvana Canevari, and T. Thigpen. "Targeting the folate receptor: diagnostic and therapeutic approaches to personalize cancer treatments." Annals of Oncology 26.10 (2015): 2034-2043 (Year: 2015).*
Yao, Houzong et al. "Methods to Design and Synthesize Antibody-Drug Conjugates (ADCs)." International journal of molecular sciences vol. 17,2 194. Feb. 2, 2016, doi:10.3390/ijms17020194 (Year: 2016).*
Drake, P., et al., "Aldehyde Tag Coupled With HIPS Chemistry Enables the Production of ADCs Conjugated Site- Specifically to Different Antibody Regions with Distinct in Vivo Efficacy and PK Outcomes", Bioconjugate Chemistry, 2014, pp. 1331-1341, vol. 25.
Grenacs, A., et al., "Copper (II) and Nickel (II) Binding Sites of Peptide Containing Adjacent Histidyl Residues", Journal of Inorganic Biochemistry, 2015, pp. 87-93, vol. 151.
Krop, I., et al., "Trastuzumab Emtansine: A Novel Antibody-Drug Conjugate for HER2-Positive Breast Cancer", Clinical Cancer Research, 2013, No. DOI:10.1158/1078-041, Publisher: American Association for Cancer Research.
Meyskens, F. L, Jr, et al., "Cancer Prevention: Obstacles, Challenges and the Road Ahead", Journal of the National Cancer Institute, 2015, Page(s) doi:10.1093/jnci/djv309, vol. 108, No. 2, Publisher: Oxford.
Strop, P., et al., "Location Matters: Site of Conjugation Modulates Stability and Pharmacokinetics of Antibody Drug Conjugates", Chemistry & Biology, Feb. 21, 2013, pp. 161-167, vol. 20.
Wang, L, et al., "Addition of the Keto Functional Group to the Genetic Code of *Escherichia coli*", PNAS, Jan. 7, 2003, pp. 56-61, vol. 100, No. 1.
Zimmerman, E., et al., "Production of Site-Specific Antibody-Drug Conjugates Using Optimized Non-Natural Amino Acids in a Cell-Free Expression System", Bioconjugate Chemistry, 2014, pp. 351-361, vol. 25.
Schneider-Merck, T., et al., Human IgG2 Antibodies against Epidermal Growth Factor Receptor Effectively Trigger Antibody-Dependent Cellular Cytotoxicity, but, in Contrast to IgG1, Only by Cells of Myeloid Lineage, J. Immunol. 2010, 184:512-520, prepublished online Nov. 30, 2009, doi: 10.4049/jimmunol.0900847.
Yao, H., et al., "Methods to Design and Synthesize Antibody-Drug Conjugates (ADCs)", International Journal of Molecular Sciences, 2016, 17, 194; doi: 10.3390/ijms 17020194.

* cited by examiner

*Primary Examiner* — Michael Szperka
*Assistant Examiner* — Lia E Taylor
(74) *Attorney, Agent, or Firm* — HULTQUIST IP; Steven J. Hultquist

(57) ABSTRACT

The present disclosure relates to an antibody-drug conjugate in which a modified antibody comprising a motif having a specific structure at the end of the antibody is conjugated to a drug via a linker, and a composition comprising the same, and more particularly to a modified antibody-drug conjugate (mADC) comprising a modified antibody that has a significantly increased conjugation yield of drug due to a motif bound to the heavy chain or light chain C-terminus of the antibody, and to a composition comprising the same.

11 Claims, 3 Drawing Sheets

Specification includes a Sequence Listing.

After Conjugation
10 % SDS-PAGE gel (R)

4 ug. 10% SDS-PAGE (R) 2016.03.25

ANTIBODY-DRUG CONJUGATE COMPRISING MODIFIED ANTIBODY

CROSS-REFERENCE TO RELATED APPLICATIONS

This is a divisional under 35 USC § 120 of U.S. patent application Ser. No. 16/088,804 filed Sep. 26, 2018, which in turn is a U.S. national phase under 35 USC § 371 of International Patent Application PCT/KR2017/003508 filed Mar. 30, 2017, claiming priority under 35 USC § 119 of Korean Patent Application 10-2016-0042269 filed Apr. 6, 2016 and of Korean Patent Application 10-2017-0040472 filed Mar. 30, 2017. The disclosures of all such applications are hereby incorporated herein by reference, in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "440 DIV_SeqListing_ST25.txt" created on Dec. 14, 2021 and is 62,517 bytes in size. The sequence listing contained in this .txt file is part of the specification and is hereby incorporated by reference herein in its entirety.

TECHNICAL FIELD

The present disclosure relates to an antibody-drug conjugate in which a modified antibody comprising a motif having a specific structure at the end of the antibody is conjugated to a drug via a linker, and a composition comprising the same, and more particularly to a modified antibody-drug conjugate (mADC) comprising a modified antibody that has a significantly increased conjugation yield of drug due to a motif bound to the heavy chain or light chain C-terminus of the antibody, and to a composition comprising the same.

BACKGROUND ART

Drugs that are used in anticancer chemotherapies often show toxicities, particularly, bone marrow toxicity, mucosal toxicity and neurotoxicity. Therefore, it is required to develop anticancer agents that show specificity for cancer cells while showing strong anticancer activity and being safer. Anticancer agents having reduced side effects while acting specifically on cancer cells have been developed in various ways.

In this respect, therapeutic agents based on antibodies that bind specifically to targets, that is, antigens that are expressed specifically in specific diseases, are currently being most actively studied among biopharmaceuticals. In particular, it is required to identify tumor-related antigens that are expressed specifically on the surface of cancer cells. Methods for diagnosing and treating tumors using antibodies that bind to these antigens to inhibit cancer cell growth or induce apoptosis, that is, anticancer antibodies, are widely used today, and their future prospects are also very bright.

Although these anticancer antibodies have very high target specificity, their effects on cancer cell killing are lower in many cases than conventional cytotoxic drugs (anticancer agents), that is, anticancer drugs. For this reason, in many cases, these anticancer antibodies are used in combination therapy with cytotoxic drugs and other drugs for inhibiting cancer cell growth. Anticancer drugs show significantly higher cytotoxicity than anticancer antibodies, but have a low level of target specificity to cancer cells, and thus show very high side effects compared to anticancer therapeutic agents. Thus, combination therapy of an anticancer antibody and an anticancer drug shows a higher therapeutic effect than individual administration of each drug, but has fundamental limitations in that the side effects of the anticancer drug always occur.

In addition, anticancer drugs have very high cytotoxicity, and for this reason, among these anticancer drugs, drugs that may be used alone as anticancer therapeutic agents are limited to taxol-based drugs or cisplatin-based drugs, which have relatively low toxicity. Most anticancer drugs are virtually impossible to prescribe as single drugs, due to their very high cytotoxicity. When an anticancer drug that cannot be used as a single therapy is conjugated with an antibody having very high target specificity for cancer cells, the anticancer drug can be delivered only to target cancer cells without side effects on normal cells. Therefore, antibody-drug conjugates are attracting attention as a method capable of increasing the therapeutic efficacy of anticancer drugs that could not previously be used.

Antibody-drug conjugates put on the market today include Adcetris®, a therapeutic agent for the treatment of Hodgkin's lymphoma, and Kadcyla®, a therapeutic agent for the treatment of metastatic breast cancer. These antibody-drug conjugates have a structure in which an antibody is conjugated to a tubulin inhibitor that binds to tubulin, an intracellular microtubule involved in the cell division process to inhibit cell division, thereby inhibiting the growth and division of cancer. The antibody-drug conjugates have either a structure in which a drug is conjugated to the lysine of an antibody (Kadcyla), or a structure in which a drug is conjugated to a cysteine group obtained by reducing a disulfide bond between a heavy chain and a heavy chain or between a heavy chain and a light chain, which maintains the structural stability of the antibody (Adcetris). In the method of conjugating the anticancer drugs used in these first-generation antibody-drug conjugates, the number of drugs conjugated per antibody cannot be controlled, and positional isomers with different sites of drug conjugation are produced even in antibody-drug conjugates having the same number of conjugated drugs. The number of drugs conjugated per antibody is a factor that influences not only the cytotoxicity of the antibody-drug conjugate, but also the stability of the antibody-drug conjugate, the possibility of aggregate formation, and the like. In general, as the number of conjugated drugs increases, the stability of the antibody itself decreases and the possibility of aggregate formation increases.

In addition, for the first-generation antibody-drug conjugates, the number of drugs conjugated per antibody cannot be controlled, and thus the number of drugs conjugated per antibody has an average value. For example, for Kadcyla, the number of drugs conjugated per antibody has a distribution of 1 to 8, the average number of drugs conjugated is 3.5. Even in antibody-drug conjugates having the same number of drugs conjugated, the characteristics of the antibody-drug conjugates may vary depending on the sites of drug conjugation. If a drug is conjugated near the Fab or near the hinge of the Fc, the stability of the antibody or the antigen-antibody reactivity can also be reduced due to a difference in its binding affinity for the antigen or the Fcγ or FcRn receptor. As the number of drugs conjugated per antibody increases, the number of positional isomers with different sites of drug conjugation also increases proportionately, and this result can have a significant impact on maintaining the consistent properties of the antibody-drug conjugates between production batches.

Thus, in recent years, various conjugation techniques for site-specific drug conjugation have been developed in order to overcome the disadvantages of the first-generation antibody-drug conjugates as described above. Genetech developed a technique for conjugating a drug using the ThioMab technology, in which a cysteine group is introduced by replacing the amino acid of an antibody, and then the drug is site-specifically conjugated to the introduced cysteine group. This showed that the antibody-drug conjugate obtained by site-specific drug conjugation had better in vivo activity than the first-generation antibody-drug conjugates (Junutula et al., Nature Biotechnology, 2008, 26, 925-932). Site-specific conjugation is a drug conjugation method employing protein enzymes having a very high substrate specificity, and has also been attempted by several companies.

It was reported that a desired number of drugs could be site-specifically conjugated to an antibody by methods, including site-specific conjugation employing formylglycine-generating enzyme (Drake et al., Bioconjugate Chemistry, 2014, 25, 1331-1341), conjugation employing glutamine transferase (Strop et al., Chemistry & Biology, 2013, 20, 161-167), and the like. However, these conjugation methods employing protein enzymes have a disadvantage in that conjugation is performed in the presence of an excessive amount of a drug at 37° C. for 72 hours or in that a high concentration of a conjugation enzyme is required.

A conjugation method employing a non-natural amino acid, which is another site-specific conjugation method, is based on a technology capable of introducing a side chain absent in a natural amino acid into a protein by synthesizing a tRNA capable of a non-natural amino acid into the protein through a mutant of tRNA synthetase (Wang et al., Proc. Natl. Acad. Sci. USA, 2003, 100, 56-61). By virtue of this method, a drug can be conjugated to a desired site by site-specific conjugation to the introduced non-natural amino acid residue (zimmerman et. Al, Bioconjugate Chem. 2014, 25, 351-361). However, this method requires a highly difficult task that controls the translation pathway through a highly advanced genetic engineering technique.

This site-specific conjugation requires a very large amount of time and cost for a site-specific conjugation reaction, because the transcription system should be modified using a complex genetic engineering technique or an excessive amount of a conjugation enzyme should be added. In view of the basic concept of antibody-drug conjugates, by which the antibody serves as a carrier that specifically delivers the anticancer drug to cancer cells and the drug should remain stably bound to the antibody until it is delivered to the cancer cells, questions cannot help being raised on whether producing an antibody-drug conjugate by use of this complicated, time-consuming and costly conjugation method is indeed necessary. A conjugation method having high economic efficiency while being capable of achieving site-specific conjugation in the production of an antibody-drug conjugate can be an excellent alternative that can overcome the limitations of not only the conventional conjugation method for producing the first-generation antibody-drug conjugates, but also the newly proposed site-specific conjugation method.

Antibody-drug conjugates exhibit significantly better in vitro and in vivo efficacies compared to conventional antibody drugs. However, the results of some clinical tests performed to use antibody-drug conjugates as first-line therapeutic agents failed to show the difference of significant clinical usefulness compared to combination therapy of a monoclonal antibody therapeutic agent and a chemical synthetic drug (roche.com/media/store/releases/med-cor-2014-12-19.htm). These results can act as a great constraint on the economic efficiency of antibody-drug conjugates, considering that antibody-drug conjugates need significantly higher therapeutic costs than synthetic drugs as well as monoclonal antibody therapeutic agents. In this respect, it appears that the aforementioned site-specific conjugation methods involve serious problems in providing economic efficiency that enables antibody-drug conjugates to be used as first-line therapeutic agents.

Under this technical background, the present inventors have recognized that there is a desperate need for the development of an antibody-drug conjugate which is produced by a site-specific conjugation reaction while being superior in terms of economic efficiency to a conventional conjugation reaction. To satisfy this need, the present inventors have developed a modified antibody comprising a peptide motif including a metal ion-binding motif, and have found that the modified antibody makes it possible to achieve site-specific conjugation and, at the same time, has a significantly better conjugation yield of drug. The present disclosure is intended to provide an antibody-drug conjugate which has excellent in vivo anticancer effects due to site-specific conjugation and, at the same time, can be produced in a more economic manner.

DISCLOSURE OF INVENTION

Technical Problem

The present disclosure has been made to solve the above-described problems, and it is an object of the present disclosure to provide an antibody having a drug binding site formed by attaching a motif having a specific structure to a parent antibody. Hereinafter, this type of antibody will be referred to as modified antibody. This modified antibody is produced by modifying a conventional modified antibody having a metal ion-binding motif, and has a higher drug conjugation yield while retaining the property of site-specific conjugation. The present disclosure also provides a method for producing an antibody-drug conjugate and an anticancer drug using this modified antibody.

Technical Solution

To achieve the above object, the present disclosure provides an antibody-drug conjugate in which a modified antibody comprising a motif, represented by the following structural formula (1), at the end of the antibody, is bound to a drug by a linker:

$$X_a\text{-}[M_{motif1}]_{n1}\text{-}X_b\text{-}[M_{motif2}]_{n2} \qquad \text{Structural Formula (1)}$$

wherein:

$M_{motif1}$ and $M_{motif2}$ each independently comprises a sequence of any one of ACGHA (SEQ ID NO: 1), AHGCA (SEQ ID NO: 2), AXGHA (SEQ ID NO: 3) and AHGXA (SEQ ID NO: 4), wherein X in SEQ ID NO: 3 or 4 comprises an amino acid residue other than cysteine;

$X_a$ and $X_b$ are each independently a peptide consisting of to 20 amino acid residues selected from the group consisting of A (alanine), S (serine), and G (glycine); and n1 and n2 are each an integer ranging from 1 to 10.

The present disclosure also provides a composition for preventing or treating cancer, which comprises the above-described antibody-drug conjugate.

BEST MODE FOR CARRYING OUT THE INVENTION

Figure 1:
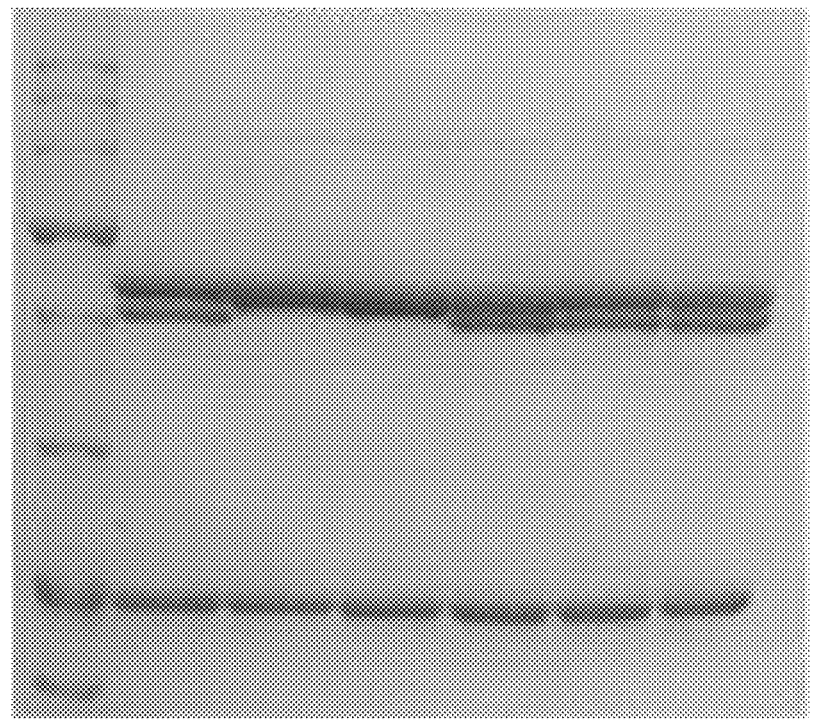
FIG. 1 shows the results of SDS-PAGE of samples obtained by conjugating MC-vc-PAB-MMAE to each of FM2, FM2b (lot no: 4390f), FM2b (lot no: 5698f), FM2a, FM2L and FM1, which are antibody variants that target folate receptor. The drug was conjugated to a cysteine-containing motif introduced into the heavy chain of the antibody, and appeared as two bands in the heavy chain near 50 kDa on SDS-PAGE.
Figure 2:
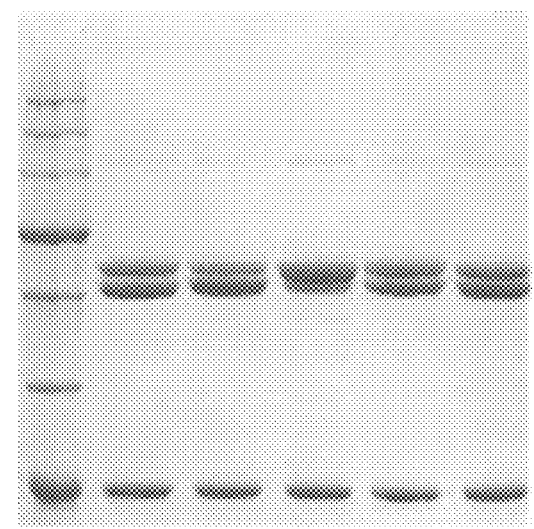
FIG. 2 shows the results of SDS-PAGE of samples obtained by conjugating br-vc-PAB-MMAE (which is a drug-linker conjugate obtained by connecting MMAE to bromoacetamide) to each of FM2, FM2b, FM2a, FM2L and FM1, which are antibody variants that target folate receptor. The drug was conjugated to a cysteine-containing motif introduced into the heavy chain of the antibody, and appeared as two bands in the heavy chain near 50 kDa on SDS-PAGE.

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

An antibody-drug conjugate requires that the anticancer drug should remain stably bound to the antibody until the anticancer drug is delivered to target cancer cells. The anticancer drug delivered to the target cancer cells should be released from the antibody and should induce the death of the cancer cells. To this end, the anticancer drug should be stably bound to the antibody by a linker, and this drug-linker structure should have sufficient cytotoxicity so that the drug will induce the death of cancer cells when it is released in the cancer cells. In addition, the drug should be site-specifically conjugated to the antibody, and the antibody-drug conjugate should have anticancer efficacy and show uniformity in its production process.

To this end, the present inventors showed that a drug could be site-specifically conjugated by introducing a peptide including a metal ion-binding motif into the C-terminus of an antibody, and that a uniform ratio of antibody-drug conjugation could be achieved (Korean Patent No. 1541764). Thus, it was shown that while the drug was site-specifically bound to the modified antibody, the characteristics of the parent antibody were maintained, and the drug-antibody conjugate could exhibit a very high target specificity and drug effect. However, due to the significantly high production cost of the drug-antibody conjugate compared to those of synthetic drugs or monoclonal antibody treatments, it is urgently required to increase the economic efficiency by increasing the conjugation yield of the drug.

Accordingly, in the present disclosure, it was attempted to demonstrate that the conjugation ratio of drug to antibody can be significantly increased by using a modified antibody comprising a peptide motif including a metal ion-binding motif, that is, according to the sequence and primary structure of the metal ion-binding motif introduced into the end of the parent antibody.

In one aspect, the present disclosure is directed to an antibody-drug conjugate in which a modified antibody comprising a motif, represented by the following structural formula (1), at the end of the antibody, is bound to a drug by a linker:

$$X_a\text{-}[M_{motif1}]_{n1}\text{-}X_b\text{-}[M_{motif2}]_{n2} \qquad \text{Structural Formula (1)}$$

wherein:

$M_{motif1}$ and $M_{motif2}$ each independently comprises a sequence of any one of ACGHA (SEQ ID NO: 1), AHGCA (SEQ ID NO: 2), ACGHA (SEQ ID NO: 3) and AHGXA (SEQ ID NO: 4), wherein X in SEQ ID NO: 3 or 4 comprises an amino acid residue other than cysteine;

$X_a$ and $X_b$ are each independently a peptide consisting of to 20 amino acid residues selected from the group consisting of A (alanine), S (serine), and G (glycine); and n1 and n2 are each an integer ranging from 1 to 10.

The motif represented by the above structural formula (1) is a peptide comprising a CGH motif which is a metal ion-binding motif. The CGH motif has a structure represented by the following formula 1:

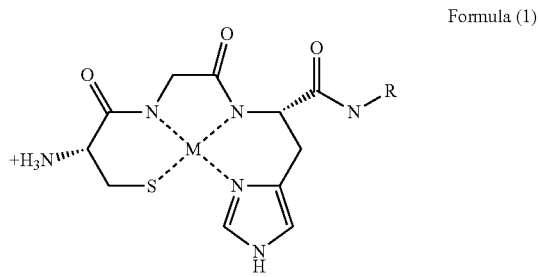

Formula (1)

wherein M represents a metal ion, and R represent an amino acid residue other than cysteine, preferably alanine.

In the motif according to the present disclosure, $M_{motif1}$ and $M_{motif2}$ each comprises ACGHA (SEQ ID NO: 1) comprising alanine located at the C-terminus and N-terminus thereof, or AXGHA (SEQ ID NO: 3) obtained by replacing the cysteine of the ACGHA with an amino acid residue other than cysteine. The motif still has the metal ion-binding property even when the positions of the N-terminus and the C-terminus of each of $M_{motif1}$ and $M_{motif2}$ are reversed, and thus AHGCA (SEQ ID NO: 2) or AHGXA (SEQ ID NO: 4) having the reversed positions of the N-terminus and the C-terminus in ACGHA (SEQ ID NO: 1) or AXGHA (SEQ ID NO: 3) falls within the scope of the $M_{motif1}$ or $M_{motif2}$ of the motif according to the present disclosure.

$M_{motif1}$ and $M_{motif2}$ in the motif according to the present disclosure may comprise the same sequence or different sequences.

In one example of the present disclosure, when the $M_{motif1}$ or $M_{motif2}$ corresponds to AXGHA or AHGXA, X in AXGHA or AHGXA may be an amino acid residue selected from the group consisting of serine (S), alanine (A), threonine (T), tyrosine (Y), aspartic acid (D), lysine (K), and phenylalanine (F).

In one example of the present disclosure, it was found that the case where $M_{motif2}$ comprises AXGHA (SEQ ID NO: 3) and X in AXGHA is an amino acid residue other than cysteine can show a higher drug conjugation ability than the case where $M_{motif2}$ comprises ACGHA. When the $M_{motif2}$ corresponds to AXGHA, X in AXGHA may be an amino acid residue other than cysteine, for example, an amino acid residue selected from the group consisting of serine (S), alanine (A), threonine (T), tyrosine (Y), aspartic acid (D), lysine (K), and phenylalanine (F).

$X_a$ is an amino acid residue sequence present at the 5' end of the motif $M_{motif1}$. In some cases, it may be a peptide located for connection with the end of the antibody. $X_a$ is a peptide consisting of 0 to 20 amino acid residues selected from the group consisting of A (alanine), S (serine), and G (glycine). If the amino acid residue number of $X_a$ is 0, the motif will not include $X_a$, and the motif $M_{motif1}$ may be bound directly to the antibody. The amino acid residue number of $X_a$ may be more than one, two, three, four, or five. For example, the amino acid residue number of $X_a$ may be 2 to 20, 2 to 18, 2 to 16, 2 to 14, 2 to 12, 2 to 10, 2 to 8, 2 to 6, 2, 3, 4, 5, 6, 7, 8, 9, or 10.

$X_b$ is a linker for connecting $M_{motif1}$ and $M_{motif2}$ to each other, and is a peptide consisting of 0 to 20 amino acid residues selected from the group consisting of A (alanine), S (serine), and G (glycine). If the amino acid residue number of $X_b$ is 0, the motif will not include $X_b$, and $M_{motif1}$ and $M_{motif2}$ may be bound directly to the antibody. The amino acid residue number of $X_b$ may be more than one, two, three, four, or five. For example, the amino acid residue number of $X_B$ may be 2 to 20, 2 to 18, 2 to 16, 2 to 14, 2 to 12, 2 to 10, 2 to 8, 2 to 6, 2, 3, 4, 5, 6, 7, 8, 9, or 10.

n1 and n2 represent the numbers of repeats of $M_{motif1}$ and $M_{motif2}$, respectively, and are each an integer ranging from 1 to 10. The n1 and n2 may each be 1, and in this case, $M_{motif1}$ and $M_{motif2}$, which comprise the sequence of any one of ACGHA (SEQ ID NO: 1), AHGCA (SEQ ID NO: 2), AXGHA (SEQ ID NO: 3) and AHGXA (SEQ ID NO: 4), may be connected to each other without the linker $X_b$ or by the linker $X_b$. For example, the $[M_{motif1}]_{n1}$-$X_b$-$[M_{motif2}]_{n2}$ structure may be ACGHAACGHA (SEQ ID NO: 5), ACGHAAHGCA (SEQ ID NO: 6), ACGHAAXGHA (SEQ ID NO: 7), ACGHAAHGXA (SEQ ID NO: 8), AHGCAAHGCA (SEQ ID NO: 9), AHGCAACGHA (SEQ ID NO: 10), AHGCAAXGHA (SEQ ID NO: 11), AHGCAAHGXA (SEQ ID NO: 12), AXGHAAXGHA (SEQ ID NO: 13), AXGHAACGHA (SEQ ID NO: 14), AXGHAAHGCA (SEQ ID NO: 15), AXGHAAHGXA (SEQ ID NO: 16), AHGXAAHGXA (SEQ ID NO: 17), AHGXAACGHA (SEQ ID NO: 18), AHGXAAHGCA (SEQ ID NO: 19), or AHGXAAXGHA (SEQ ID NO: 20), if the linker $X_b$ is not present, and motifs essentially comprising C (cysteine) for conjugation with the drug may be selected as $M_{motif1}$ and $M_{motif2}$.

If $X_b$ is present, a peptide consisting of 1 to 20 amino acid residues may additionally be included at position 6 ($6^{th}$) of the 5' end of each of the above-described amino acid sequences. In this case, X may be selected from the group consisting of serine (S), alanine (A), threonine (T), tyrosine (Y), aspartic acid (D), lysine (K), and phenylalanine (F).

The $[M_{motif1}]_{n1}$-$X_b$-$[M_{motif2}]_{n2}$ structure may be ACGHAASGHA (SEQ ID NO: 21), ACGHAAHGSA (SEQ ID NO: 22), AHGCAASGHA (SEQ ID NO: 23), AHGCAAHGSA (SEQ ID NO: 24), ASGHAASGHA (SEQ ID NO: 25), ASGHAACGHA (SEQ ID NO: 26), ASGHAAHGCA (SEQ ID NO: 27), ASGHAAHGSA (SEQ ID NO: 28), AHGSAAHGSA (SEQ ID NO: 29), AHGSAACGHA (SEQ ID NO: 30), AHGSAAHGCA (SEQ ID NO: 31), or AHGSAASGHA (SEQ ID NO: 32), which comprises serine at position X of SEQ ID NOS: 7, 8, 11 to 20 comprising X, for example, if X is serine (S) when the linker $X_b$ is not present.

The $[M_{motif1}]_{n1}$-$X_b$-$[M_{motif2}]_{n2}$ structure may be ACGHAAAGHA (SEQ ID NO: 33), ACGHAAHGAA (SEQ ID NO: 34), AHGCAAAGHA (SEQ ID NO: 35), AHGCAAHGAA (SEQ ID NO: 36), AAGHAAAGHA (SEQ ID NO: 37), AAGHAACGHA (SEQ ID NO: 38), AAGHAAHGCA (SEQ ID NO: 39), AAGHAAHGAA (SEQ ID NO: 40), AHGAAAHGAA (SEQ ID NO: 41), AHGAAACGHA (SEQ ID NO: 42), AHGAAAHGCA (SEQ ID NO: 43), or AHGAAAAGHA (SEQ ID NO: 44) when, for example, X is alanine (A) if the linker $X_b$ is not present.

The $[M_{motif1}]_{n1}$-$X_b$-$[M_{motif2}]_{n2}$ structure may be ACGHAATGHA (SEQ ID NO: 45), ACGHAAHGTA (SEQ ID NO: 46), AHGCAATGHA (SEQ ID NO: 47), AHGCAAHGTA (SEQ ID NO: 48), ATGHAATGHA (SEQ ID NO: 49), ATGHAACGHA (SEQ ID NO: 50), ATGHAAHGCA (SEQ ID NO: 51), ATGHAAHGTA (SEQ ID NO: 52), AHGTAAHGTA (SEQ ID NO: 53), AHGTAACGHA (SEQ ID NO: 54), AHGTAAHGCA (SEQ ID NO: 55), or AHGTAATGHA (SEQ ID NO: 56), for example, if X is threonine (T) when the linker $X_b$ is not present.

The $[M_{motif1}]_{n1}$-$X_b$-$[M_{motif2}]_{n2}$ structure may be ACGHAAYGHA (SEQ ID NO: 57), ACGHAAHGYA (SEQ ID NO: 58), AHGCAAYGHA (SEQ ID NO: 59), AHGCAAHGYA (SEQ ID NO: 60), AYGHAAYGHA (SEQ ID NO: 61), AYGHAACGHA (SEQ ID NO: 62), AYGHAAHGCA (SEQ ID NO: 63), AYGHAAHGYA (SEQ ID NO: 64), AHGYAAHGYA (SEQ ID NO: 65), AHGYAACGHA (SEQ ID NO: 66), AHGYAAHGCA (SEQ ID NO: 67), or AHGYAAYGHA (SEQ ID NO: 68), for example, if X is tyrosine (Y) when the linker $X_b$ is not present.

The $[M_{motif1}]_{n1}$-$X_b$-$[M_{motif2}]_{n2}$ structure may be ACGHAADGHA (SEQ ID NO: 69), ACGHAAHGDA (SEQ ID NO: 70), AHGCAADGHA (SEQ ID NO: 71), AHGCAAHGDA (SEQ ID NO: 72), ADGHAADGHA (SEQ ID NO: 73), ADGHAACGHA (SEQ ID NO: 74), ADGHAAHGCA (SEQ ID NO: 75), ADGHAAHGDA (SEQ ID NO: 76), AHGDAAHGDA (SEQ ID NO: 77), AHGDAACGHA (SEQ ID NO: 78), AHGDAAHGCA (SEQ ID NO: 79), or AHGDAADGHA (SEQ ID NO: 80) when, for example, X is aspartic acid (D) if the linker $X_b$ is not present.

The [M$_{motif1}$]$_{n1}$-X$_b$-[M$_{motif2}$]$_{n2}$ structure may be ACGHAAKGHA (SEQ ID NO: 81), ACGHAAHGKA (SEQ ID NO: 82), AHGCAAKGHA (SEQ ID NO: 83), AHGCAAHGKA (SEQ ID NO: 84), AKGHAAKGHA (SEQ ID NO: 85), AKGHAACGHA (SEQ ID NO: 86), AKGHAAHGCA (SEQ ID NO: 87), AKGHAAHGKA (SEQ ID NO: 88), AHGKAAHGKA (SEQ ID NO: 89), AHGKAACGHA (SEQ ID NO: 90), AHGKAAHGKA (SEQ ID NO: 91), or AHGKAAKGHA (SEQ ID NO: 92), for example, if X is lysine (K) when the linker X$_b$ is not present.

The [M$_{motif1}$]$_{n1}$-X$_b$-[M$_{motif2}$]$_{n2}$ structure may be ACGHAAFGHA (SEQ ID NO: 93), ACGHAAHGFA (SEQ ID NO: 94), AHGCAAFGHA (SEQ ID NO: 95), AHGCAAHGFA (SEQ ID NO: 96), AFGHAAFGHA (SEQ ID NO: 97), AFGHAACGHA (SEQ ID NO: 98), AFGHAAHGCA (SEQ ID NO: 99), AFGHAAHGFA (SEQ ID NO: 100), AHGFAAHGFA (SEQ ID NO: 101), AHGFAACGHA (SEQ ID NO: 102), AHGFAAHGFA (SEQ ID NO: 103), or AHGFAAFGHA (SEQ ID NO: 104), for example, if X is phenylalanine (F) when the linker X$_b$ is not present.

If X$_b$ is present, a peptide consisting of 1 to 20 amino acid residues may additionally be included at position 6 of the 5' end of each of the above-described amino acid sequences of SEQ ID NOS: 5 to 104. In this case, X may be selected from the group consisting of serine (S), alanine (A), threonine (T), tyrosine (Y), aspartic acid (D), lysine (K), and phenylalanine (F). In this case, X may be selected from the group consisting of serine (S), alanine (A), threonine (T), tyrosine (Y), aspartic acid (D), lysine (K), and phenylalanine (F).

n1 and n2 may each be 2 or greater. For example, if n1 and n2 are each 2 and M$_{motif1}$ and M$_{motif2}$ comprise the same amino acid sequence, M$_{motif1}$ and M$_{motif2}$ may comprise two repeats of the sequence of any one of ACGHA (SEQ ID NO: 1), AHGCA (SEQ ID NO: 2), AXGHA (SEQ ID NO: 3) and AHGXA (SEQ ID NO: 4). If M$_{motif1}$ and M$_{motif2}$ comprise different amino acid sequences, they may comprise, for example, two repeats of each of ACGHA and AHGCA, ACGHA and AXGHA, ACGHA and AHGXA, AHGCA and ACGHA, AHGCA and AXGHA, AHGCA and AHGXA, AXGHA and ACGHA, AXGHA and AHGCA, AXGHA and AHGXA, AHGXA and ACGHA, AHGXA and AHGCA, or AHGXA and AXGHA, respectively. If n1 and n2 are each an integer ranging from 3 to 10, M$_{motif1}$ and M$_{motif2}$ may comprise 3 to 10 repeats of either the same sequence corresponding to any one of, or different sequences selected from among from, ACGHA (SEQ ID NO: 1), AHGCA (SEQ ID NO: 2), AXGHA (SEQ ID NO: 3) and AHGXA (SEQ ID NO: 4).

Preferably, n1 and n2 may each be 1, and the linker X$_b$ may not be present. In this case, the motif may comprise one or more sequences selected from the group consisting of SEQ ID NOS: 5 to 104.

The motif may be bound to the heavy-chain or light-chain C-terminus of the antibody, particularly the heavy-chain C-terminus, thereby providing a modified antibody having a significantly increased conjugation yield of the drug or a drug conjugate comprising the same. By increasing the conjugation yield of the drug, the production yield of the antibody-drug conjugate can be increased. The drug conjugated in high yield may be delivered specifically to target cancer cells by means of the modified antibody, thereby increasing therapeutic effects. In addition, due to the high conjugation yield of the antibody-drug conjugate, the production cost of the antibody-drug conjugate as a therapeutic agent can be reduced.

The motif can be fused directly to the parent antibody by an amide bond. Alternatively, the terminal functional group of the motif can be chemically bound to the terminal functional group of the parent antibody. Alternatively, the motif can also be bound to the parent antibody in a linker mediated manner by using a linker that links the terminal functional group of the motif and a drug.

The linker may be configured to connect a specific residue in the motif to the drug, and may have a reactive site having an electrophilic group that reacts with a nucleophilic residue (e.g., cysteine) present on the motif of the modified antibody. The linker may comprise, for example, a reactive functional group, an amino acid, and a self-cleavage spacer, which bind to the motif.

The functional group may be i) a maleimide group, an acetamide group, or derivatives thereof, ii) an aziridine group, an aryl halide group, an acryloyl group, or derivatives thereof, or iii) an alkylating reactive group, an arylating reactive group, pyridyl disulfide, thionitrobenzoic acid, or derivatives thereof. Specifically, the linker may be in the form of i) a maleimide polyimide group or its derivative-valine-citrulline-para-aniline benzoic acid (PABA); or ii) an acetamide group or its derivative-valine-citrulline-para-aniline benzoic acid (PABA), but is not limited thereto.

Binding of the cysteine residue to a drug by the linker may be performed by using a known method, for example, alkylation, disulfide exchange or transthioesterification reaction. This enables the drug to be conjugated to the antibody by the thiol group of the cysteine residue in the motif.

In an embodiment of the present disclosure, a maleimide group that is generally used for linking thiol and a linker is used to specifically conjugate a drug to cysteine, because the nucleophilic reactivity of the thiol group of a cysteine residue for the maleimide group is about 1,000 times higher than that of other amino acid functional group present in a protein, for example, the amino group or N-terminal amino group of a lysine residue. Thus, it can be seen that in the case of a modified antibody-drug conjugate based on a maleimide group or its derivative, or an acetamide group or its derivative, for example, a bromoacetamide group or an iodoacetamide group, cysteine is bound to the drug by a thioether bond.

The antibody may be one or more selected from the group consisting of a monoclonal antibody, a bispecific antibody, a chimeric antibody, a human antibody, and a humanized antibody. In addition, modified antibodies such as bispecific antibodies, or fragments of the antibodies, may also be used in the present disclosure. As used herein, the term "fragment of the antibody" refers to a fragment that at least retains a binding affinity to an antigen. Examples of the antibody fragment include single-chain antibodies, diabodies, triabodies, tetrabodies, Fab fragments, F(ab')$_2$ fragments, Fd, scFv, domain antibodies, minibodies, single-chain antibodies (scAb), derivatives of antibody constant regions, and artificial antibodies based on protein scaffolds.

In some embodiments, the antibody may be selected from the group consisting of IgA, IgD, IgE, IgG, and IgM.

The antibody may have a binding affinity and specificity for specifically, cancer-specific antigens, cell surface receptor proteins, cell surface proteins, transmembrane proteins, signaling proteins, cell survival regulators, cell proliferation regulators, molecules associated with tissue development or differentiation, lymphokines, cytokines, molecules involved in cell cycle regulation, molecules involved in vasculogenesis, or molecules associated with angiogenesis. For example, the antibody may have a binding affinity for one or more targets selected from the group consisting of, but are not limited to:
(1) BMPRIB (bone morphogenetic protein receptor-type IB; Genbank Accession No. NM_001203);
(2) E16 (LAT1, SLC7A5; Genbank Accession No. NM_003486);
(3) STEAP1 (six transmembrane epithelial antigen of prostate; Genbank Accession No. NM_012449);
(4) 0772P (CA125, MUC16; Genbank Accession No. AF361486);
(5) MPF (MPF, MSLN, SMR, megakaryocyte potentiating factor, mesothelin; Genbank Accession No. NM_005823);
(6) Napi3b (NAPI-3B, NPTIIb, SLC34A2, solute carrier family 34 (sodium phosphate), member 2, type II sodium-dependent phosphate transporter 3b; Genbank Accession No. NM_006424);
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B; Genbank Accession No. AB040878);
(8) PSCA hlg (2700050C12Rik, C530008O16Rik, RIKEN cDNA 2700050C12, RIKEN cDNA 2700050C12 gene; Genbank Accession No. AY358628);
(9) ETBR (Endothelin type B receptor; Genbank Accession No. AY275463);
(10) MSG783 (RNF124, hypothetical protein FLJ20315; Genbank Accession No. NM_017763);
(11) STEAP2 (HGNC 8639, IPCA-1, PCANAP1, STAMP1, STEAP2, STMP, prostate cancer associated gene 1, prostate cancer associated protein 1, six-transmembrane epithelial antigen of prostate 2, six-transmembrane prostate protein; Genbank Accession No. AF455138);
(12) TrpM4 (BR22450, FLJ20041, TRPM4, TRPM4B, transient receptor potential cation channel, subfamily M, member 4; Genbank Accession No. NM_017636);
(13) CRIPTO (CR, CR1, CRGF, CRIPTO, TDGF1, teratocarcinoma-derived growth factor; Genbank Accession No. NP_003203 or NM_003212);
(14) CD21 (CR2 (Complement receptor 2) or C3DR (C3d/Epstein Barr virus receptor) or Hs.73792; Genbank Accession No. M26004);
(15) CD79b (CD79B, CD79β, IGb (immunoglobulin-associated beta), B29; Genbank Accession No. NM_000626);
(16) FcRH2 (IFGP4, IRTA4, SPAP1A (SH2 domain containing phosphatase anchor protein 1a), SPAP1B, SPAP1C; Genbank Accession No. NM_030764);
(17) HER2 (Genbank Accession No. M11730);
(18) ErbB receptor selected from among EGFR, HER3 and HER4
(19) NCA (Genbank Accession No. M18728);
(20) MDP (Genbank Accession No. BC017023);
(21) IL20R α (Genbank Accession No. AF184971);
(22) Brevican (Genbank Accession No. AF229053);
(23) EphB2R (Genbank Accession No. NM_004442);
(24) ASLG659 (Genbank Accession No. AX092328);
(25) PSCA (Genbank Accession No. AJ297436);
(26) GEDA (Genbank Accession No. AY260763);
(27) BAFF-R (B cell-activating factor receptor, BLyS receptor, BR3; NP_443177.1);
(28) CD22 (B-cell receptor CD22-B isoform; NP-001762.1);
(29) CD79a (CD79A, CD79α, immunoglobulin-associated alpha, a B cell-specific protein that covalently interacts with Ig beta (CD79B) and forms a complex on the surface with IgM molecules, transduces a signal involved in B-cell differentiation; Genbank Accession No. NP_001774.1);
(30) CXCR5 (Burkitt's lymphoma receptor 1, a G protein-coupled receptor that is activated by the CXCL 13 chemokine, functions in lymphocyte migration and humoral defense, plays a role in HIV-2 infection and regarded for development of AIDS, lymphoma, myeloma, and leukemia; Genbank Accession No. NP_001707.1);
(31) HLA-DOB (Beta subunit of MHC class II molecule (la antigen) that binds peptides and presents them to CD4+ T lymphocytes; Genbank Accession No. NP_002111.1);
(32) P2X5 (Purinergic receptor P2X ligand-gated ion channel 5, an ion channel gated by extracellular ATP, may be involved in synaptic transmission and neurogenesis, and its deficiency may contribute to the pathophysiology of idiopathic detrusor instability; Genbank Accession No. NP_002552.2);
(33) CD72 (B-cell differentiation antigen CD72, Lyb-2; Genbank Accession No. NP_001773.1);
(34) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis; Genbank Accession No. NP_005573.1);
(35) FcRH1 (Fc receptor-like protein 1, a putative receptor for the immunoglobulin Fc domain that contains C2 type Ig-like and ITAM domains, may have a role in B-lymphocyte differentiation; Genbank Accession No. NP_443170.1);
(36) IRTA2 (Immunoglobulin superfamily receptor translocation associated 2, a putative immunoreceptor with possible roles in B cell development and lymphomagenesis; deregulation of the gene by translocation occurs in some B cell malignancies; Genbank Accession No. NP_112571.1);
(37) TENB2 (putative transmembrane proteoglycan, related to the EGF/heregulin family of growth factors and follistatin; Genbank Accession No. AF179274);
(38) MAGE-C1/CT7 (protein overexpressed in testicular cancer);
(39) androgen receptor, PTEN, human kallikrein-related peptidase 3 (protein overexpressed in prostate cancer);
(40) CD20;
(41) CD30;
(42) CD33;
(43) CD52;
(44) EpCam;
(45) CEA;
(46) gpA33;
(47) Mucins;
(48) TAG-72;
(49) Carbonic anhydrase IX;
(50) PSMA;
(51) folate receptor (protein family overexpressed by FOLR gene. It has a binding affinity for folic acid, and intracellularly delivers 5-methyltetrahydrofolate);
(52) gangliosides (GD2, GD3, GM2);
(53) hydrate/saccharide Lewis-Y;

(54) VEGF;
(55) VEGFR;
(56) aVb3;
(57) a5b1;
(58) ERB3;
(59) c-MET;
(60) EphA3;
(61) TRAIL-R1, TRAIL-R2;
(62) RANKL;
(63) FAP; and
(64) Tenascin.

In an embodiment of the present disclosure, an antibody (Farletuzumab) binding to a folate receptor comprising a heavy chain of SEQ ID NO: 115 and a light chain of SEQ ID NO: 116 was used as a parent antibody. Various modified antibodies with various peptide motif sequences and arrangements were produced by introducing metal ion-binding motifs into the heavy-chain end of the parent antibody, and then the difference in the conjugation yield of drug between the modified antibodies was measured. The modified antibody may comprise one or more heavy chains selected from the group consisting of SEQ ID NOS: 117 to 121.

In addition, in another example of the present disclosure, an antibody (Trastuzumab) specifically binding to Her2 was used as a parent antibody. Various modified antibodies with various peptide motif sequences and arrangements were produced by introducing metal ion-binding motifs into the heavy-chain end of the parent antibody, and then the difference in the conjugation yield of drug between the modified antibodies was measured.

As a result, in antibody-drug conjugates according to the present disclosure, it was shown that when the motif was introduced into Farletuzumab and Trastuzumab, these antibodies had the equivalent level of drug conjugation yield. Therefore, the motif according to the present disclosure may be used as a platform technology for conjugating a drug to an antibody in the production of antibody-drug conjugates, regardless of the type of antibody.

In one embodiment, the antibody may comprise both the variable region of the parent antibody or the modified antibody and the CH1, CH2 and CH3 of IgG2 or IgG4. For example, the antibody may use the VH and VL of Farletuzumab, or Trastuzumab, or its modified antibody, and may comprise the CH1, CH2 and CH3 of IgG2 or IgG4. For example, the variable region of the Farletuzumab antibody may comprise the heavy-chain variable region of SEQ ID NO: 122 and/or the light-chain variable region of SEQ ID NO: 123.

In another embodiment, the antibody may comprise both the Fab of the parent antibody or the modified antibody and the Fc of IgG2 or IgG4. Specifically, it may comprise a fusion of the Fab region of Farletuzumab, Trastuzumab, or its modified antibody with the Fc region of IgG2 or IgG4. For example, the Fab of the Farletuzumab antibody may comprise the heavy-chain variable region of SEQ ID NO: 122 and the light-chain variable region of SEQ ID NO: 124 comprising the CH1 and/or SEQ ID NO: 124. The Trastuzumab antibody may comprise the heavy chain of SEQ ID NO: 127 and/or the light chain of SEQ ID NO: 128.

A drug that is bound to the modified antibody of the present disclosure may be any drug having disease therapeutic effects. Particularly, it is preferably a cancer therapeutic drug having the effect of inhibiting the proliferation of tumor cells.

The drug may be conjugated to a cysteine group or a serine group of a motif introduced into the end of the modified antibody.

Specifically, a drug that may be used in the modified antibody-drug conjugate of the present disclosure comprises any compound, moiety or group that has a cytotoxic or cytostatic effect, and examples thereof include: (i) chemotherapeutic agents capable of functioning as microtubulin inhibitors, mitotic inhibitors, topoisomerase inhibitors, or DNA intercalators; (ii) protein toxins capable of functioning as enzymes; (iii) micro-RNA (miRNA), siRNA, or shRNA, which can inhibit the expression of a specific oncogene; and (iv) radioisotopes.

Such a drug may be one or more selected from the group consisting of, but is not limited thereto, maytansinoid, auristatin, aminopterin, actinomycin, bleomycin, talisomycin, camptothecin, $N^8$-acetyl spermidine, 1-(2 chloroethyl)-1,2-dimethyl sulfonyl hydrazide, esperamicin, etoposide, 6-mercaptopurine, dolastatin, trichothecene, calicheamicin, taxane, methotrexate, vincristine, vinblastine, doxorubicin, melphalan, mitomycin A, mitomycin C, chlorambucil, duocamycin, nucleolytic enzymes, toxins of bacterial, plant or animal origin, cisplatin, irinotecan, paclitaxel, and docetaxel.

In some embodiments, the drug may comprise one or more nucleophilic groups selected from the group consisting of amine, thiol, hydroxyl, hydrazide, oxime, hydrazine, thiosemicarbazone, hydrazine carboxylate, and aryl hydrazide groups, which can react with the linker and an electrophilic group on the linker reagent to form a covalent bond.

In another aspect, the present disclosure provides a therapeutic composition comprising the above-described antibody-drug conjugate as an active ingredient. In the composition, the drug conjugated to a modified antibody-drug conjugate may be a cytotoxic agent, a cell proliferation inhibitor, a chemotherapeutic agent, an immune inhibitor, an anti-inflammatory agent or the like, but is not limited thereto. In cancer therapy, the use of the antibody-drug conjugate for local delivery of a drug that kills or inhibits tumor cells allows the targeted delivery of the drug moiety into tumor cells by antibody-antigen interactions and the intracellular accumulation of the drug moiety.

The present disclosure also provides a method of inhibiting the proliferation of target cells with cancer, autoimmune, inflammatory or infectious disease by contacting the target cells using a modified antibody-drug conjugate as an active ingredient.

Cancer that can be treated according to the present disclosure may be one or more selected from among, but is not limited to, liver cancer, gastric cancer, breast cancer, colon cancer, bone cancer, pancreatic cancer, head and neck cancer, uterine cancer, ovarian cancer, rectal cancer, esophageal cancer, small intestine cancer, anal cancer, fallopian tube cancer, endometrial cancer, cervical cancer, vaginal cancer, vulva cancer, Hodgkin's disease, prostate cancer, bladder cancer, renal cancer, ureter cancer, renal cell carcinoma, renal pelvis cancer, and cancer of the central nervous system. In a specific example, proliferation of folate receptor-amplified cancer KB cells can be inhibited by bringing the modified antibody-drug conjugate into contact with the cells in vitro. Therefore, it is evident that the inventive method of inhibiting the proliferation of target cells using the modified antibody-drug conjugate as an active ingredient has the effect of killing cells related to the above-described disease or reducing and inhibiting the proliferation rate of the cells.

Unless otherwise defined, the technical or scientific terms as used herein have the same meanings as understood by those having ordinary knowledge in the technical field to which the present disclosure pertains. Also, the detailed description of the same construction and effect as those of the prior art will be omitted herein.

EXAMPLES

Hereinafter, the present disclosure will be described in further detail with reference to examples. It will be obvious to a person having ordinary skill in the art that these examples are not to be construed to limit the scope of the present disclosure, and various modifications and changes can be made within the technical idea and scope of the present disclosure.

Example 1

Construction of Expression Vector pAV4

For expression vector cloning, a pAV4 was used, which was developed by improving the parent vector pSGHV0 (GenBank Accession No. AF285183) according to the intended use so as to be capable of being used in antibody production in the industrial field. When a human protein is expressed using bacteria such as *E. coli*, it is overexpressed in the cells, but there are proteins difficult to obtain as physiologically active substances. Thus, the parent vector is a research vector developed for the purpose of extracellularly expressing the physiologically active protein of interest using animal cells and easily purifying the expressed protein. However, since there are various restrictions on the use of this vector in industrial production, this vector was improved so that it could be used in the industrial field, in order to use a high expression level, which is the biggest advantage of this vector, in production. In addition, for antibodies, two proteins (a heavy chain and a light chain) should be co-expressed, and for this reason, a vector suitable for this purpose was developed.

Example 2

Construction of Vectors for Parent Antibody Having Binding Affinity for Folate Receptor and Modified Antibody Comprising Modified Ion-Binding Motif ACGHA To construct a parent antibody (Fwt) vector having binding affinity for folate receptor, a cDNA encoding a heavy chain of SEQ ID NO: 125 and a cDNA encoding a light chain of SEQ ID NO: 126 were synthesized as codon-optimized sequences so that their expressions in CHO cells would be maximized. These genes were cloned into the XhoI/NotI and ApaI/SmaI of the pAV4 vector, respectively, thereby constructing a parent antibody vector (pFwt).

TABLE 1

| Amino acid sequence of Fwt antibody | | |
|---|---|---|
| | Sequences | SED ID NOS: |
| Heavy chain | EVQLVESGGGVVQPGRSLRLSCSASGETFSGYGLSWVRQAPGKGLEWVAMIS SGGSYTYYADSVKGRFAISRDNAKNTLFLQMDSLRPEDTGVYFCARHGDDPA WFAYWGQGTPVTVSSASTKGPSVFPLAPSSKSTSGGTAALGCLVKDYFPEPV TVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPGK | SED ID NO: 115 |
| Light chain | DIQLTQSPSSLSASVGDRVTITCSVSSSISSNNLHWYQQKPGK APKPWIYGTSNLASGVPSRFSGSGSGTDYTFTISSLQPEDIAT YYCQQWSSYPYMYTFGQGTKVEIKRTVAAPSVFIFPPSDEQLK SGTASVVCLLNNFYPREAKVQWKVDNALQSGNSQESVTEQDSK DSTYSLSSTLTLSKADYEKHKVYACEVTHQGLSSPVTKSFNRG EC | SED ID NO: 116 |

2-1: Construction of Modified Antibody FM2 from Folate Receptor-Binding Parent Antibody Fwt To construct the modified antibody FM2 (Fwt-ACGHAACGHA (SED ID NO: 5), FM2) having two metal ion-binding motifs (ACGHA) from Fwt, PCR amplification was performed using the parent antibody Fwt vector (pFwt) as a template, an XhoI-Q5-F forward primer (5'-GCTCCTCGAGGCCACCATGGGATGGAGCTGT ATCATCC-3': SED ID NO: 105) and an M2 reverse primer (5'-CCATGCGGCCGCTCATTTAGGCATGGCCA CAAGCAGCATGGCCACAGGCACCCGGAGACAGG-GAGAGGC-3': SED ID NO: 106). The amplified nucleotide was cleaved with two restriction enzymes (XhoI and NotI) at the ends, and ligated with the expression vector pFwt having XhoI/NotI cleavage sites, thereby constructing a modified antibody vector (pFM2).

2-2: Construction of Folate Receptor-Binding Modified Antibody FM1

To construct the modified trastuzumab antibody FM1 (Fwt-GGGACGHA, pFM1) having only one metal ion-binding motif (ACGHA), PCR amplification was performed by the site-directed mutagenesis (Enzynomics co Ltd., EzChange Site-directed mutagenesis kit, Ez004S) method using the above-constructed FM2 as a template, a forward primer (5'-GCTCCTCGAGGCCACCATGGGATG-GAGCTGT ATCATCC-3': SED ID NO: 107) and a reverse primer (5'-CCATGCGGCCGCTCATTTAGGCATGGCC ACAAGCA CCTC CACCACCCGGAGACAGGGAGA-3': SED ID NO: 108). The amplified nucleotide was cleaved with two restriction enzymes (XhoI and NotI) at the ends, and ligated with the expression vector pFwt having XhoI/NotI cleavage sites, thereby constructing a modified antibody vector (pFM1).

2-3: Construction of Folate Receptor-Binding Modified Antibody FM2L

To construct the modified antibody FM2L (Fwt-ACGHAGGGACGHA, pFM2L) comprising metal ion-binding motifs (ACGHA) connected by a linker consisting of 3 amino acid residues, PCR was performed by the site-directed mutagenesis (Enzynomics co Ltd., EzChange Site-directed mutagenesis kit, Ez004S) method using the above-constructed modified antibody FM2 as a template, a forward primer (5'-GCTCCTCGAGGCCACCATGG-GATGGAGCTGTATCATCC-3': SED ID NO: 109) and a reverse primer (5'-CCATGCGGCCGCTCATTTAGG-CATGGCCACAAGCACCTCCACCAGCATGGC-CACAGGCACC CGGAGACAGGGAGAGGC-3': SED ID NO: 110), thereby adding a glycine linker between two metal ion-binding motifs. The amplified nucleotide was cleaved with two restriction enzymes (XhoI and NotI) at the ends, and ligated with the expression vector pFwt having XhoI/NotI cleavage sites, thereby constructing a modified antibody vector (pFM2L).

2-4: Construction of Folate Receptor-Binding Modified Antibody FM2a

To construct a modified antibody FM2a (Fwt-ASGHAACGHA (SED ID NO: 26), pFM2a) having only one metal ion-binding motif by replacing the inner cysteine in ACGHAACGHA (SEQ ID NO: 5), which consists of two metal ion-binding motifs present in the FM2 modified antibody, with serine, PCR was performed using the above-constructed modified antibody FM2 as a template, a forward primer (5'-GCTCCTCGAGGCCACCATGGGATG-GAGCTGT ATCATCC-3': SED ID NO: 111) and a reverse primer (5'-CAGATTGCGGCCGCTCATTAGGCATGGC-CACAAGCAGCATGGCCTG AGGCACCCGGA-GACAGG-3': SED ID NO: 112), thereby replacing the inner cysteine with serine. The amplified nucleotide was cleaved with two restriction enzymes (XhoI and NotI) at the ends, and ligated with the expression vector pFwt having XhoI/NotI cleavage sites, thereby constructing a modified antibody vector (pFM2a)

2-5: Construction of Folate Receptor-Binding Modified Antibody FM2b

To construct a modified antibody FM2b (Fwt-ACGHAASGHA (SED ID NO: 21), pFM2b) having only one metal ion-binding motif by replacing the outer cysteine in ACGHAACGHA, which consists of two metal ion-binding motifs present in the FM2 modified antibody, with serine, PCR was performed by the site-directed mutagenesis (Enzynomics co Ltd., EzChange Site-directed mutagenesis kit, Ez004S) method using the above-constructed modified antibody FM2 as a template, a forward primer (5'-GCTCCTCGAGGCCACCATGGGATGGAGCTGTAT-CATCC-3': SED ID NO: 113) and a reverse primer (5'-CAGATTGCGGCCGCTCATTAGGCATGGCCTGAAG-CAGCATGGCCACA GGCACCCGGAGACAGG-3': SED ID NO: 114), thereby replacing the outer cysteine with serine. The amplified nucleotide was cleaved with two restriction enzymes (XhoI and NotI) at the ends, and ligated with the expression vector pFwt having XhoI/NotI cleavage sites, thereby constructing a modified antibody vector (pFM2b)

TABLE 2

| FM antibody | | |
|---|---|---|
| | Sequences | SED ID NOS: |
| FM2 heavy chain | EVQLVESGGGVVQPGRSLRLSCSASGETFSGYGLSWVRQAPGKGLEWVAMISS GGSYTYYADSVKGRFAISRDNAKNTLFLQMDSLRPEDTGVYFCARHGDDPAWF AYWGQGTPVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGACGHAACGHA | SED ID NO: 117 |
| FM2a heavy chain | EVQLVESGGGVVQPGRSLRLSCSASGETFSGYGLSWVRQAPGKGLEWVAMISS GGSYTYYADSVKGRFAISRDNAKNTLFLQMDSLRPEDTGVYFCARHGDDPAWF AYWGQGTPVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGASGHAACGHA | SED ID NO: 118 |
| FM2b heavy chain | EVQLVESGGGVVQPGRSLRLSCSASGETFSGYGLSWVRQAPGKGLEWVAMISS GGSYTYYADSVKGRFAISRDNAKNTLFLQMDSLRPEDTGVYFCARHGDDPAWF AYWGQGTPVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGACGHAASGHA | SED ID NO: 119 |
| FM1 heavy chain | EVQLVESGGGVVQPGRSLRLSCSASGETFSGYGLSWVRQAPGKGLEWVAMISS GGSYTYYADSVKGRFAISRDNAKNTLFLQMDSLRPEDTGVYFCARHGDDPAWF AYWGQGTPVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK | SED ID NO: 120 |

TABLE 2-continued

FM antibody

| | Sequences | SED ID NOS: |
|---|---|---|
| | VDKKVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGGGGACGHA | |
| FM2L heavy chain | EVQLVESGGGVVQPGRSLRLSCSASGETFSGYGLSWVRQAPGKGLEWVAMISS<br>GGSYTYYADSVKGRFAISRDNAKNTLFLQMDSLRPEDTGVYFCARHGDDPAWF<br>AYWGQGTPVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGACGHAGGGACGHA | SED ID NO: 121 |

Example 3

Expression and Purification of Folate Receptor-Binding Parent Antibody Fwt and Modified Antibodies Using Chinese hamster ovary cells (CHO-K1), protein expression of Fwt and its metal ion-binding motif modified antibodies (FM1, FM2, FM2L, FM2a, and FM2b), constructed in Example 2, was analyzed. CHO-K1 was cultured in DMEM (Dulbecco's Modified Eagle Media) containing 10% FBS (Fetal Bovine Serum) and an antibiotic in a 5% $CO_2$ incubator at 37° C. On day before introduction of Fwt and its modified antibody expression vectors, the cells were inoculated into a 100 mm culture dish at a concentration of $5 \times 10^6$ cells/ml and cultured, and then a mixture of 800 µl of FBS-free DMEM and 10 µg of Fwt or each modified antibody expression vector was kept at room temperature for 1 minute, and then mixed with 20 µg of PEI (polyethylenimine, linear, Polysciences Inc (Cat. no: 23966, MW-25,000)), followed by incubation at room temperature for about 10 to 15 minutes. At this time, the cells cultured before one day were washed with PBS, and 6 ml of fresh DMEM medium was added thereto. The Fwt or its modified antibody expression vector, incubated at room temperature for 10 to 15 minutes, was added to the culture dish. On the next day, the cells were washed with PBS, and FBS-free IMDM medium (Cat. No 12200-028, Gibco, Iscove's Modified Dulbecco's Medium) was added thereto, followed by analysis of protein expression.

The Fwt and its metal ion-binding motif modified antibodies were purified as follows. Specifically, to purify the Fwt and its metal ion-binding motif modified antibodies secreted into the cell culture media, each of the culture media was centrifuged, and the cells were removed, after which the supernatant was collected, injected into an HiTrap Protein A HP (GE Healthcare, USA) column equilibrated with equilibration buffer. Then, the supernatant was sufficiently washed with equilibration buffer, after which the pH was altered by addition of glycine buffer (100 mM Glycine, pH 2.8), thereby eluting the protein. The resulting solution was dialyzed against phosphate buffer, and then concentrated using Vivaspin20 (Sartorius, USA), and finally, highly purified protein was obtained.

Example 4

Production of Antibody-Drug Conjugates by Reaction between Modified Antibody of Fwt, Maleimide Group and Cysteine In the present disclosure, MMAE was conjugated to the modified antibody Fwt, thereby producing an FMx (metal ion-binding motif variant of Fwt)-MMAE conjugate. Monomethyl Auristatin E (known as MMAE; see Formula 2 below), a conjugatable derivative of Auristatin, is linked to a maleamide group, which binds selectively to a thiol group, via valine-citurulline, which is degraded by protease in cells, and para-aniline benzoic acid (PABA) which is a self-cleavage spacer group Formula 2

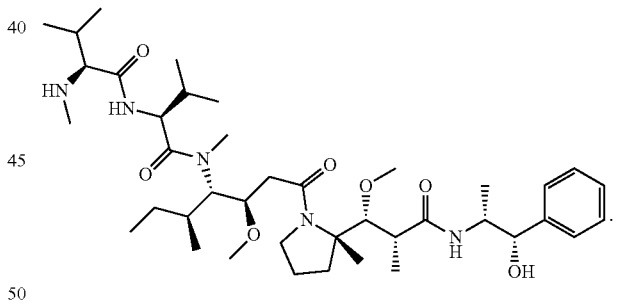

This linked structure is generally referred to as MC (maleimido caproic acid)-VC (valine-citurulline)-PAB-MMAE, and Auristatin, a highly cytotoxic compound, is known to have an $IC_{50}$ value of 200 to 300 pM in cell proliferation inhibition assay.

In the present disclosure, 3 equivalents of the reducing agent TCEP was added per equivalent of the purified modified antibody and allowed to react at 4° C. for 30 minutes so as to reduce the thiol group, and then 3 equivalents of MC-vc-PAB-MMAE was added thereto and allowed to react at room temperature for 2 hours. The reaction was stopped by addition of an excess of cysteine, and an excess of MC-vc-PAB-MMAE and TCEP were removed by centrifugation, filtration and dialysis in phosphate buffered saline, thereby producing resulting purified FMx-MC-vc-PAB-MMAE.

The yield of conjugation to the heavy chain of each modified antibody is shown in Table 3 below.

TABLE 3

Yield of conjugation to each modified antibody via maleimide group

| | Modified antibody | | | | |
|---|---|---|---|---|---|
| | FM1 | FM2 | FM2a | FM2b | FM2L |
| Conjugation yield | 62.7% | 64.1% | 64.5% | 97.5% | 66.3% |

As can be seen in Table 3 above, the yield of conjugation of the drug to the heavy chain did significantly differ between the modified antibodies. The modified antibodies, including FM1, FM2, FM2a and FM2L, showed a conjugation yield of about 63 to 66% under drug conjugation conditions, whereas FM2b showed a very high drug conjugation yield of 97.5%. FM2b showed substantially similar conjugation yields in samples collected from two different transient transfection batches.

Example 5

Production of Antibody-Drug Conjugates by Reaction between Modified Antibody of Fwt, Bromoacetamide Group and Cysteine In this Example, antibody-drug conjugates were produced by conjugation to the thiol group of cysteine via a bromoacetamide group. Bromoacetamide was bound to MMAE via valine-citurulline, which is degraded by protease in cells, and para-aniline benzoic acid (PABA) which is a self-cleavage spacer group, and MMAE was conjugated to each modified antibody by binding between bromoacetamide and a thiol group. The produced conjugate was named br (bromo acetamide)-VC (valine-citurulline)-PAB-MMAE.

In the present disclosure, 3 equivalents of the reducing agent TCEP was added per equivalent of the purified modified antibody and allowed to react at 4° C. for 30 minutes so as to reduce the thiol group, and then 3 equivalents of br-vc-PAB-MMAE was added thereto and allowed to react at 37° C. for 2 hours. The reaction was stopped by addition of an excess of cysteine, and an excess of br-vc-PAB-MMAE and TCEP were removed by centrifugation, filtration and dialysis in phosphate buffered saline, thereby producing resulting purified FMx-acetamide-vc-PAB-MMAE.

The yield of conjugation to the heavy chain of each modified antibody is shown in Table 4 below.

TABLE 4

Yield of conjugation to each modified antibody via bromoacetamide group

| | Modified antibody | | | | |
|---|---|---|---|---|---|
| | FM1 | FM2 | FM2a | FM2b | FM2L |
| Conjugation yield | 42% | 44% | 38% | 73% | 49% |

As can be seen in Table 4 above, in the yield of conjugation of the drug to the heavy chain between the modified antibodies, FM2b shows a significantly excellent conjugation yield compared to other modified antibodies. Even in the conjugation reaction via iodoacetamide group, FM2b shows a significantly excellent conjugation yield compared to other modified antibodies.

TABLE 5

Yield of conjugation to each modified antibody via iodoacetamide group

| | Modified antibody | | | | |
|---|---|---|---|---|---|
| | FM1 | FM2 | FM2a | FM2b | FM2L |
| Conjugation yield | 51% | 53% | 44% | 80% | 55% |

Example 6

Production of Modified Trastuzumab Antibodies

According to the method used in Example 2 above, a modified antibody was produced by introducing a metal ion-binding motif including cysteine into the C-terminus of trastuzumab.

6-1. Construction of Modified Antibody HM2 from Trastuzumab

To construct the modified antibody HM2 (HR-ACGHAACGHA (SED ID NO: 5), HM2) having two metal ion-binding motifs (ACGHA) from trastuzumab, PCR amplification was performed using the parent antibody trastuzumab vector (pHR) as a template, an XhoI-Q5-F forward primer (5'-GCTCCTCGAGGCCACCATGG-GATGGAGCTGT ATCATCC-3': SED ID NO: 111) and an M2 reverse primer (5'-CCATGCGGCCGCTCATTTAGG-CATGGCCA CAAGCAGCATGGCCACAGGCACCCG-GAGACAGGGAGAGGC-3': SED ID NO: 112). The amplified nucleotide was cleaved with two restriction enzymes (XhoI and NotI) at the ends, and ligated with the expression vector pHR having XhoI/NotI cleavage sites, thereby constructing a modified antibody vector (pHM2).

6-2. Construction of Modified Antibody HM2a from Trastuzumab

To construct a modified antibody HM2a (HR-ASGHAACGHA (SED ID NO: 26), pHM2a) having only one metal ion-binding motif by replacing the inner cysteine in ACGHAACGHA (SEQ ID NO: 5), which consists of two metal ion-binding motifs present in the HM2 modified antibody, with serine, PCR was performed using the above-constructed modified antibody HM2 as a template, a forward primer (5'-GCTCCTCGAGGCCACCATGGGATG-GAGCTGT ATCATCC-3': SED ID NO: 111) and a reverse primer (5'-CAGATTGCGGCCGCTCATTAGGCATGGC-CACAAGCAGCATGGCCTG AGGCACCCGGA-GACAGG-3': SED ID NO: 112), thereby replacing the inner cysteine with serine. The amplified nucleotide was cleaved with two restriction enzymes (XhoI and NotI) at the ends, and ligated with the expression vector pHR having XhoI/NotI cleavage sites, thereby constructing a modified antibody vector (pHM2a).

6-3. Construction of Modified Antibody HM2b from Trastuzumab

To construct a modified antibody HM2b (HR-ACGHAASGHA (SED ID NO: 21), pHM2b) having only one metal ion-binding motif by replacing the outer cysteine in ACGHAACGHA, which consists of two metal ion-binding motifs present in the HM2 modified antibody, with serine, PCR was performed by the site-directed mutagenesis (Enzynomics co Ltd., EzChange Site-directed mutagenesis kit, Ez004S) method using the above-constructed modified antibody HM2 as a template, a forward primer (5'-GCTCCTCGAGGCCACCATGGGATGGAGCTGTAT-CATCC-3': SED ID NO: 113) and a reverse primer (5'-

CAGATTGCGGCCGCTCATTAGGCATGGCCTGAAGCAG-CATGGCCACA GGCACCCGGAGACAGG-3': SED ID NO: 114), thereby replacing the outer cysteine with serine. The amplified nucleotide was cleaved with two restriction enzymes (XhoI and NotI) at the ends, and ligated with the expression vector pHR having XhoI/NotI cleavage sites, thereby constructing a modified antibody vector (pHM2b).

Example 7

Expression and Purification of Modified Trastuzumab Antibodies

Using Chinese hamster ovary cells (CHO-K1), protein expression of the modified trastuzumab antibodies (HM2, HM2a, HM2b), constructed in Example 6, was analyzed. CHO-K1 was cultured in DMEM (Dulbecco's Modified Eagle Media) containing 10% FBS (Fetal Bovine Serum) and an antibiotic in a 5% $CO_2$ incubator at 37° C. On day before introduction of Fwt and its modified antibody expression vectors, the cells were inoculated into a 100 mm culture dish at a concentration of $5 \times 10^6$ cells/ml and cultured, and then a mixture of 800 μl of FBS-free DMEM and 10 μg of Fwt or each modified antibody expression vector was kept at room temperature for 1 minute, and then mixed with 20 μg of PEI (polyethylenimine, linear, Polysciences Inc (Cat. no: 23966, MW of about 25,000)), followed by incubation at room temperature for about 10 to 15 minutes. At this time, the cells cultured before one day were washed with PBS, and 6 ml of fresh DMEM medium was added thereto. The Fwt or its modified antibody expression vector, incubated at room temperature for 10 to 15 minutes, was added to the culture dish. On the next day, the cells were washed with PBS, and FBS-free IMDM medium (Cat. No 12200-028, Gibco, Iscove's Modified Dulbecco's Medium) was added thereto, followed by analysis of protein expression.

The modified antibodies were purified as follows. Specifically, to purify the modified antibodies secreted into the cell culture media, each of the culture media was centrifuged, and the cells were removed, after which the supernatant was collected, injected into an HiTrap Protein A HP (GE Healthcare, USA) column equilibrated with equilibration buffer. Then, the supernatant was sufficiently washed with equilibration buffer, after which the pH was altered by addition of glycine buffer (100 mM Glycine, pH 2.8), thereby eluting the protein. The resulting solution was dialyzed against phosphate buffer, and then concentrated using Vivaspin20 (Sartorius, USA), and finally, highly purified protein was obtained.

Example 8

Production of Antibody-Drug Conjugates by Conjugation of MC-vc-PAB-MMAE to Modified Trastuzumab Antibodies In the present disclosure, HMx (metal ion-binding motif variant of trastuzumab)-MMAE conjugates were produced by conjugating MMAE to the modified trastuzumab antibodies produced in Examples 6 and 7. In the present disclosure, 3 equivalents of the reducing agent TCEP was added per equivalent of the purified modified antibody and allowed to react at 4° C. for 30 minutes so as to reduce the thiol group, and then 2.5 equivalents of MC-vc-PAB-MMAE was added thereto and allowed to react at room temperature for 2 hours. The reaction was stopped by addition of an excess of cysteine, and an excess of MC-vc-PAB-MMAE and TCEP were removed by centrifugation, filtration and dialysis in phosphate buffered saline, thereby producing resulting purified FMx-MC-vc-PAB-MMAE.

The yield of conjugation to the heavy chain of each modified antibody is shown in Table 6 below.

TABLE 6

| Yield of conjugation to each modified antibody via maleimide group | | | |
|---|---|---|---|
| | Modified antibody | | |
| | HM2 | HM2a | HM2b |
| Conjugation yield | 55.5% | 62.4% | 85.5% |

As can be seen in Table 6 above, the yield of conjugation of the drug to the heavy chain did significantly differ between the modified antibodies. The modified antibodies, HM2 and HM2a, showed a conjugation yield of about 55 to 62% under the same drug conjugation conditions, whereas HM2b showed a very high drug conjugation yield of 85.5%. These results indicate that even when the sequence of M2b is introduced into not only Farletuzumab, but also other antibodies, the conjugation yield is also high.

Example 9

Production of Modified Antibodies by Replacement of Serine in M2b (ACGHAASGHA; SEQ ID NO: 21) Sequence From the Examples above, it could be seen that M2b (ACGHAASGHA) obtained by replacing the inner cysteine in the metal ion-binding motif M2 (ACGHAACGHA) with serine showed a significantly higher drug conjugation ability than the M2 sequence. In order to examine whether this serine replacement site shows the same effect even in replacement of other amino acids, modified antibodies were produced by replacing this site with various amino acid residues.

TABLE 7

| Modified antibodies obtained by replacing serine site of M2b sequence with other amino acid residues | |
|---|---|
| Modified antibodies | Metal ion-binding motif sequence of C-terminus |
| M2b or M2b-S | ACGHAASGHA (SEQ ID NO: 21) |
| M2b-A | ACGHAAAGHA (SEQ ID NO: 33) |
| M2b-T | ACGHAATGHA (SEQ ID NO: 45) |
| M2b-Y | ACGHAAYGHA (SEQ ID NO: 57) |
| M2b-D | ACGHAADGHA (SEQ ID NO: 69) |
| M2b-K | ACGHAAKGHA (SEQ ID NO: 81) |
| M2b-F | ACGHAAFGHA (SEQ ID NO: 93) |

Each of the modified antibodies having the C-terminal sequences shown in Table 7 above was introduced into FM2b or FM2b-S, thereby producing modified antibodies, including FM2b-A, FM2b-T, FM2b-Y, FM2b-D, FM2b-K and FM2b-F.

Example 10

Production of Antibody-Drug Conjugates by Conjugation of MC-vc-PAB-MMAE to FM2b Modified Antibodies In the present disclosure, FM2b-X-MMAE conjugates were produced by conjugating MMAE to the modified antibody FM2b-X (X=A, T, Y, D, K, or F) produced in Example 9. In the present disclosure, 3 equivalents of the reducing agent TCEP was added per equivalent of the purified modified antibody and allowed to react at 4° C. for 30 minutes so as to reduce the thiol group, and then 2.5 equivalents of MC-vc-PAB-MMAE was added thereto and allowed to react at room temperature for 2 hours. The reaction was stopped by addition of an excess of cysteine, and an excess of MC-vc-PAB-MMAE and TCEP were removed by centrifugation, filtration and dialysis in phosphate buffered saline, thereby producing resulting purified FM2b-X-MC-vc-PAB-MMAE.

The yield of conjugation to the heavy chain of each modified antibody is shown in Table 8 below.

TABLE 8

DAR2 Yield upon Conjugation of MC-vc-PAB-MMAE to FM2b-X Modified Antibodies

| | \multicolumn{7}{c}{Modified antibody} | | | | | | |
|---|---|---|---|---|---|---|---|
| | FM2b | FM2b-A | FM2b-T | FM2b-Y | FM2b-D | FM2b-K | FM2b-F |
| Conjugation yield | 72.8% | 62.5% | 69% | 74.5% | 58.9% | 75.3% | 72.9% |

As can be seen in Table 8 above, even when the inner serine site of the M2b sequence ACGHAASGHA was replaced with other amino acid residues, the results similar to those shown by FM2b were obtained.

Example 11

Purification of Antibody-Drug Conjugate Having DAR of 2

The modified antibody-drug conjugates produced in Example 4 above had different numbers of drugs conjugated per modified antibody (drug-to-antibody ratio; DAR), and for this reason, it would not be easy to compare the cytotoxicity of the drug in vitro. Thus, in order to purify modified antibody-drug conjugates having the same DAR, modified antibody-drug conjugates were purified by hydrophobic chromatography. Using phenyl column chromatography, modified antibody-drug conjugates having a DAR of 2 were purified. The column was equilibrated with buffer (containing 10 mM sodium succinate, 0.5M NaCl, pH 5.0), and then each modified antibody-drug conjugate was injected into the column. The column was washed with the same buffer, and then the buffer containing 30% acetonitrile was added thereto, and the modified antibody-drug conjugate was eluted according to the DAR. The eluted modified antibody-drug conjugate was subjected to dialysis in buffer (containing 10 mM sodium succinate, 30 mM sucrose, pH 6.0).

Example 12

Test for In Vitro Stability of Antibody-Drug Conjugates

As described in Examples 9, 10 and 11 above, FM2b-S-D2, FM2b-F-D2, FM2b-K-D2 and FM2b-Y-D2, which are antibody-drug conjugates comprising two MC-vc-PAB-MMAE drugs, were produced. Each of the produced antibody-drug conjugates was incubated at temperatures of 25° C. and 50° C., the change in the number of drugs conjugated and the change in aggregation were measured.

For each antibody-drug conjugate, 12 test samples were prepared at each of concentrations of 1 mg/mL and 110 µL. For each antibody-drug conjugate, changes in the DAR and the monomer purity were measured while 6 samples were stored at 25° C. and the remaining 6 samples were stored at 60° C. for 0, 1, 3, 5, 7 and 14 days. At 25° C., a decrease in DAR2 content of about 1.5-2% was observed in each sample, and a decrease in monomer purity of about 0.3-4% was observed in each sample, but the difference in DAR2 content and monomer purity between the samples was not significant. The changes in DAR2 content and monomer purity, observed at 50° C., were greater than the values observed at 25° C., but the difference between the samples was not significant. This suggests that the differences between the antibody variants were not significant.

TABLE 9

Monomer contents of FM2b-S-D2, FM2b-F-D2, FM2b-K-D2 and FM2b-Y-D2 on days 0, 1, 3, 5, 7 and 15 under storage conditions of 25° C. and 50° C.

| Storage temperature | Sample | Day 0 | Day 1 | Day 3 | Day 5 | Day 7 | Day 15 |
|---|---|---|---|---|---|---|---|
| 25° C. | FM2b-S-D2 | 97.6 | 97.6 | 97.2 | 96.4 | 95.6 | 95.1 |
| | FM2b-F-D2 | 97 | 97.8 | 97.2 | 96.6 | 96.1 | 95 |
| | FM2b-K-D2 | 97.6 | 97.6 | 97.3 | 96.6 | 96.1 | 96.3 |
| | FM2b-Y-D2 | 96.7 | 96.6 | 97 | 95.8 | 95.4 | 94.9 |
| 50° C. | FM2b-S-D2 | 97.6 | 93.9 | 88.8 | 82.8 | 79.1 | 68.9 |
| | FM2b-F-D2 | 97 | 93.7 | 86.9 | 80.9 | 76.9 | 63.5 |
| | FM2b-K-D2 | 97.6 | 93.9 | 87.7 | 81.8 | 77.8 | 66.8 |
| | FM2b-Y-D2 | 96.7 | 93.9 | 88.4 | 82.7 | 77.9 | 66.6 |

TABLE 10

DAR2 contents of FM2b-S-D2, FM2b-F-D2, FM2b-K-D2 and FM2b-Y-D2 on days 0, 1, 3, 5, 7 and 15 under storage conditions of 25° C. and 50° C.

| Storage temperature | DAY | Day 0 | Day 1 | Day 3 | Day 5 | Day 7 | Day 15 |
|---|---|---|---|---|---|---|---|
| 25° C. | FM2b-S-D2 | 98.9 | 98.6 | 98.6 | 98.2 | 98.4 | 98.1 |
|  | FM2b-F-D2 | 98.2 | 98.4 | 98.4 | 98.2 | 98.3 | 97.9 |
|  | FM2b-K-D2 | 97.9 | 97.4 | 97.5 | 97.3 | 97.3 | 97 |
|  | FM2b-Y-D2 | 97.6 | 97.6 | 97.4 | 96.6 | 95.5 | 93.2 |
| 50° C. | FM2b-S-D2 | 98.9 | 97.1 | 93.6 | 91.8 | 90.7 | 87.9 |
|  | FM2b-F-D2 | 98.2 | 96.5 | 93.2 | 89.4 | 88.3 | 85.1 |
|  | FM2b-K-D2 | 97.9 | 96.2 | 94.6 | 91.8 | 90.8 | 88.9 |
|  | FM2b-Y-D2 | 97.6 | 95.8 | 91.3 | 89.4 | 87.6 | 84.4 |

Example 13

Test for In Vitro Cell Growth Inhibition

To compare the in vitro cell growth inhibition abilities of the modified antibody-drug conjugates, a cell growth inhibition test was performed using KB-cells overexpressing folate receptor. KB-cells were diluted in 10% FBS-containing DMEM/F12 medium, and then 100 μl of the cell dilution was added to each well of a 96-well plate at a density of $1 \times 10^4$ cells/well. Next, the well plate was incubated in an incubator under 5% carbon dioxide at 37° C. for 24 hours to attach the cells to the plate. Each test sample was diluted in medium, and then added to each well to concentrations of 6.45 nM, 3.23 nM, 1.61 nM, 0.806 nM, 0.403 nM, 0.202 nM, 0.101 nM, 0.0504 nM, 0.0252 nM and 0.0126 nM, and medium (without drug) was also added to a control well. After 5 days of incubation, 20 μl/well of CellTiter 96-AQueous One Solution reagent [MTS-based assay; MTS forms purple formazan by dehydrogenase of living cells, and growth is measured by the amount of purple formazan produced] was added to each well, and then incubated in an incubator at 37° C. for 2 hours. The cell lysate was measured by an absorption spectrometer at an O.D. of 490 nm, thereby determining viability (%).

13-1: Test for Comparison of Cell Growth Inhibitory Activity Between FM2-D2 and FM2b-D2 (or FM2b-S-D2)

The parent antibody Fwt, FM2-D2 (a modified antibody (FM2)-drug (MMAE) conjugate having a DAR of 2) and FM2b-D2 (a modified antibody (FM2b)-drug (MMAE) having a DAR of 2), obtained by conjugating MMAE in the above Examples and performing purification to have the same DAR, were prepared, and KB cells were treated with each of the prepared conjugates, after which the cell growth inhibitory activity of the drug was compared between the conjugates.

Figure 3:
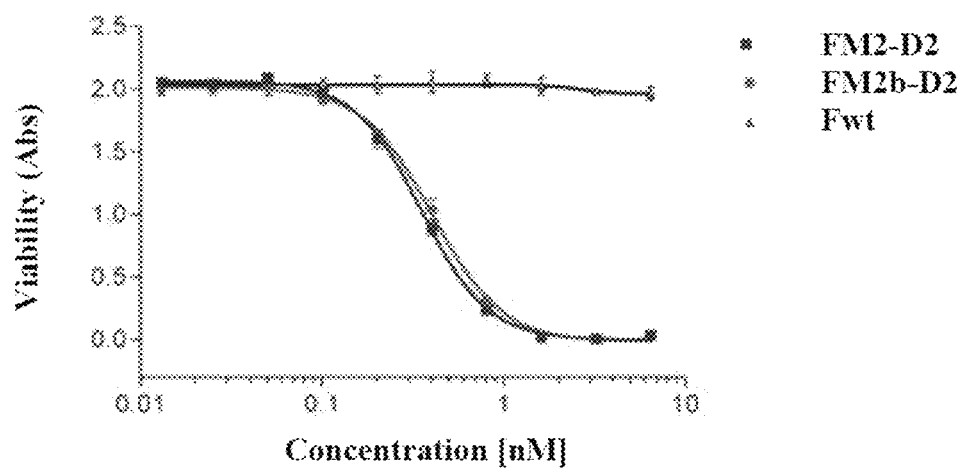
FIG. 3 shows the results of a cell growth inhibition assay performed using KB-cells overexpressing folate receptor. It compares cell growth inhibitory activity between the parent antibody Fwt, the modified antibody-drug conjugate FM2-D2 (a modified antibody (FM2)-drug (MMAE) conjugate having a DAR of 2), and FM2b-D2 (or FM2b-S-D2) (a modified antibody (FM2b-S)-drug (MMAE) conjugate having a DAR of 2). FM2-D2 and FM2b-D2 show almost the same intracellular activity.

As can be seen in FIG. 3, the antibody-drug conjugates (FM2-D2 and FM2b-D2) showed significantly better anticancer effects than the parent antibody. FM2-D2 and FM2b-D2 showed almost the same inhibitory effect against cancer cell growth. These results indicate that when the modified antibody-drug conjugates have then same DAR, there is no difference in cancer cell inhibitory activity between the modified antibodies, FM2 and FM2b.

13-2: Test for Comparison of Cell Growth Inhibitory Activity Between FM2-D2 and FM2b-D2 (or FM2b-S-D2)

To compare cell growth inhibitory activity between antibody-drug conjugates based on FM2b-S and other variants, MC-vc-PAB-MMAE was conjugated to each of FM2b-S, -F and -Y variants, and then the conjugates were purified to have the same DAR, after which KB cells were treated with each of the conjugates, and then the cell growth inhibitory activity of the drug was compared between the conjugates.

Figure 4:
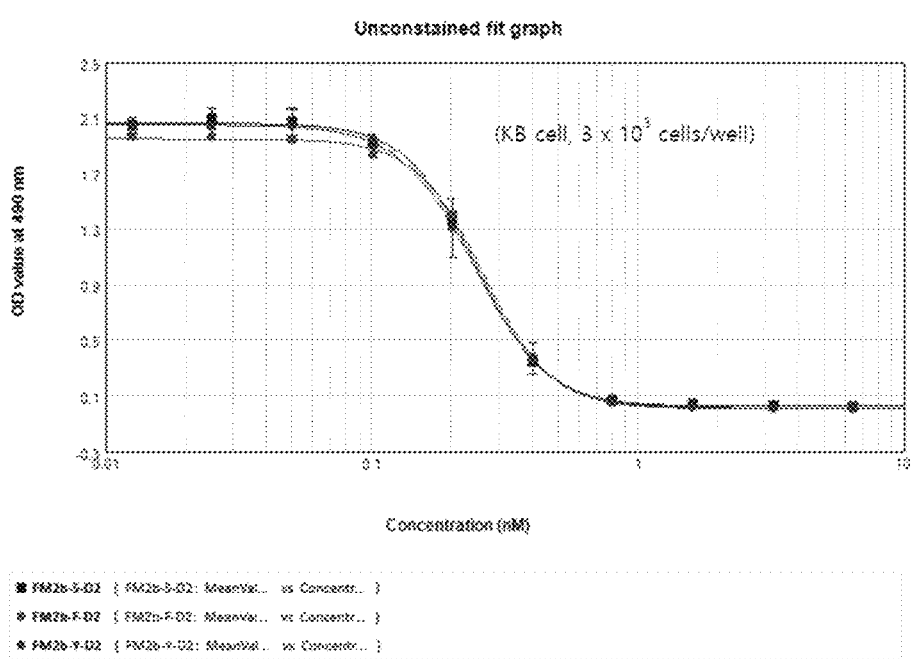
FIG. 4 shows the results of a cell growth inhibition assay performed using KB-cells overexpressing folate receptor. It shows cell growth inhibitory activity between FM2b-S-D2, FM2b-F-D2, and FM2b-Y-D2. FM2b-S-D2, FM2b-F-D2, and FM2b-Y-D2 show almost the same intracellular activity.
Figure 5:
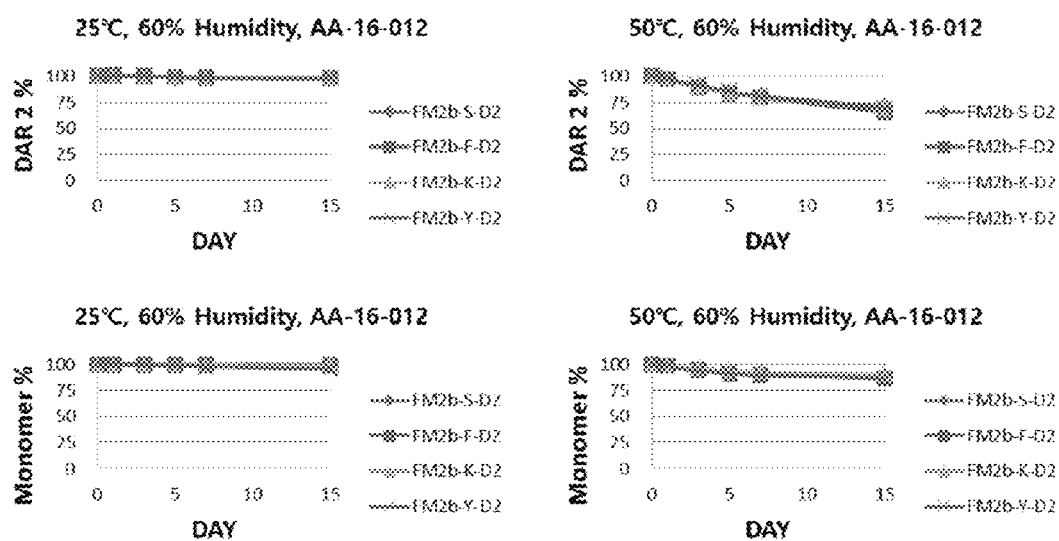
FIG. 5 shows the results of measuring changes in the number of drugs conjugated (DAR) and aggregate formation after storing FM2b-S-D2, FM2b-F-D2, FM2b-K-D2 and FM2b-Y-D2 at 25° C. and 50° C. for 0, 1, 3, 5, 7 and 14 days. At 25° C., changes in DAR and monomer were hardly observed, but at 50° C., it was observed that the content of DAR2 decreased and an aggregate was formed with time. However, differences in DAR change and aggregate formation between the variants were not observed.

As can be seen in FIG. 4, FM2b-S-D2, FM2b-F-D2 and FM2b-Y-D2 shows almost the same cell growth inhibitory activity. The measured $IC_{50}$ values were 0.25 nM for FM2b-S-D2, 0.26 nM for FM2b-F-D2, and 0.24 nM for FM2b-Y-D2. These results indicate that there is no difference in cancer cell growth inhibitory activity between the antibody-drug conjugates based on the antibody variants obtained by replacing the serine of FM2b-S with each of phenylalanine and tyrosine.

These results show that when an antibody-drug conjugate is produced using the antibody including the M2b sequence, it shows a significantly better yield of drug conjugation compared to other modified antibodies, while the anticancer activity thereof has no difference from the anticancer activities of other modified antibodies. In addition, it could be seen that even when the serine site in the M2b sequence ACGHA-ASGHA was replaced with other amino acid residues, there was no difference in the conjugation yield, stability or anticancer activity of the drug. This suggests that when the motif ACGHA-AXGHA (X is an amino acid other than cysteine) as used in FM2b or HM2b is introduced into the end of the heavy chain of an antibody, the modified antibody has a significantly better conjugation yield, making it possible to produce an antibody-drug conjugate in a more efficient and economic manner.

INDUSTRIAL APPLICABILITY

The antibody-drug conjugate produced by the antibody variants according to the present disclosure can increase the conjugation yield of the drug, thereby increasing the productivity of the antibody-drug conjugate. In addition, a drug conjugated to the end of an antibody does not hinder the structural stability of the parent antibody, so that the intrinsic antigen specificity and structural stability of the parent antibody can be maintained, and the drug conjugated to the antibody can be delivered specifically to cancer cells owing to a high antigen specificity of the parent antibody.

Although the present disclosure has been described in detail with reference to the specific features, it will be apparent to those skilled in the art that this description is only for a preferred embodiment and does not limit the scope of the present disclosure. Thus, the substantial scope of the present disclosure will be defined by the appended claims and equivalents thereof.

What is claimed is:

1. An antibody-drug conjugate in which a modified antibody comprising a motif, represented by the following structural formula (1), at an end of the antibody, is bound to a drug by a linker:

$$X_a\text{-}[M_{motif1}]_{n1}\text{-}X_b\text{-}[M_{motif2}]_{n2} \quad \text{Structural Formula (1)}$$

wherein:
$M_{motif1}$ is ACGHA (SEQ ID NO: 1) or AHGCA (SEQ ID NO: 2), and $M_{motif2}$ is AXGHA (SEQ ID NO: 3) or AHGXA (SEQ ID NO: 4), wherein X in SEQ ID NO: 3 or 4 is an amino acid residue other than cysteine (C), serine (S), alanine (A), threonine (T), tyrosine (Y), aspartic acid (D), lysine (K), or phenylalanine (F), or
$M_{motif1}$ is AXGHA (SEQ ID NO: 3) or AHGXA (SEQ ID NO: 4), wherein X in SEQ ID NO: 3 or 4 is an amino acid residue other than cysteine (C), serine (S), alanine (A), threonine (T), tyrosine (Y), aspartic acid (D), lysine (K), or phenylalanine (F), and $M_{motif2}$ is ACGHA (SEQ ID NO: 1) or AHGCA (SEQ ID NO: 2);
$X_a$ and $X_b$ independently are each a peptide consisting of 0 to 20 amino acid residues selected from the group consisting of A (alanine), S (serine), and G (glycine); and
n1 and n2 are each an integer ranging from 1 to 10.

2. The antibody-drug conjugate of claim 1, wherein the motif is introduced to the heavy-chain C-terminus of the antibody.

3. The antibody-drug conjugate of claim 1, wherein the linker comprises a reactive functional group, which bind to the motif, an amino acid, and a self-cleavage spacer.

4. The antibody-drug conjugate of claim 1, wherein the drug is one or more selected from among maytansinoid, auristatin, aminopterin, actinomycin, bleomycin, talisomycin, camptothecin, $N^8$-acetyl spermidine, 1-(2 chloroethyl)-1,2-dimethyl sulfonyl hydrazide, esperamicin, etoposide, 6-mercaptopurine, dolastatin, trichothecene, calicheamicin, taxane, methotrexate, vincristine, vinblastine, doxorubicin, melphalan, mitomycin A, mitomycin C, chlorambucil, duocamycin, nucleolytic enzymes, toxins of bacterial, plant or animal origin, cisplatin, irinotecan, paclitaxel, and docetaxel.

5. The antibody-drug conjugate of claim 1, wherein the antibody is one or more selected from the group consisting of a monoclonal antibody, a bispecific antibody, a chimeric antibody, a human antibody, and a humanized antibody.

6. The antibody-drug conjugate of claim 1, wherein the antibody is selected from the group consisting of IgA, IgD, IgE, IgG, and IgM.

7. The antibody-drug conjugate of claim 1, wherein the antibody has a binding affinity and specificity for cancer-specific antigens, cell surface receptor proteins, cell surface proteins, transmembrane proteins, signaling proteins, cell survival regulators, cell proliferation regulators, molecules associated with tissue development or differentiation, lymphokines, cytokines, molecules involved in cell cycle regulation, molecules involved in vasculogenesis, or molecules associated with angiogenesis.

8. The antibody-drug conjugate of claim 1, wherein the antibody has a binding affinity for one or more targets selected from the group consisting of:
(1) BMPRIB (bone morphogenetic protein receptor-type IB; Genbank Accession No. NM_001203);
(2) E16 (LAT1, SLC7A5; Genbank Accession No. NM_003486);
(3) STEAP1 (six transmembrane epithelial antigen of prostate; Genbank Accession No. NM_012449);
(4) 0772P (CA125, MUC16; Genbank Accession No. AF361486);
(5) MPF (MPF, MSLN, SMR, megakaryocyte potentiating factor, mesothelin; Genbank Accession No. NM_005823);
(6) Napi3b (NAPI-3B, NPTIIb, SLC34A2, solute carrier family 34 (sodium phosphate), member 2, type II sodium-dependent phosphate transporter 3b; Genbank Accession No. NM_006424);

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B; Genbank Accession No. AB040878);

(8) PSCA hlg (2700050C12Rik, C530008016Rik, RIKEN cDNA 2700050C12, RIKEN cDNA 2700050C12 gene; Genbank Accession No. AY358628);

(9) ETBR (Endothelin type B receptor; Genbank Accession No. AY275463);

(10) MSG783 (RNF124, hypothetical protein FLJ20315; Genbank Accession No. NM_017763);

(11) STEAP2 (HGNC_8639, IPCA-1, PCANAP1, STAMP1, STEAP2, STMP, prostate cancer associated gene 1, prostate cancer associated protein 1, six-transmembrane epithelial antigen of prostate 2, six-transmembrane prostate protein; Genbank Accession No. AF455138);

(12) TrpM4 (BR22450, FLJ20041, TRPM4, TRPM4B, transient receptor potential cation channel, subfamily M, member 4; Genbank Accession No. NM_017636);

(13) CRIPTO (CR, CR1, CRGF, CRIPTO, TDGF1, teratocarcinoma-derived growth factor; Genbank Accession No. NP_003203 or NM_003212);

(14) CD21 (CR2 (Complement receptor 2) or C3DR (C3d/Epstein Barr virus receptor) or Hs.73792; Genbank Accession No. M26004);

(15) CD79b (CD79B, CD79β, IGb (immunoglobulin-associated beta), B29; Genbank Accession No. NM_000626);

(16) FcRH2 (IFGP4, IRTA4, SPAP1A (SH2 domain containing phosphatase anchor protein 1a), SPAP1B, SPAP1C; Genbank Accession No. NM_030764);

(17) HER2 (Genbank Accession No. M11730);

(18) ErbB receptor selected from among EGFR, HER3 and HER4

(19) NCA (Genbank Accession No. M18728);

(20) MDP (Genbank Accession No. BC017023);

(21) IL20R α (Genbank Accession No. AF184971);

(22) Brevican (Genbank Accession No. AF229053);

(23) EphB2R (Genbank Accession No. NM_004442);

(24) ASLG659 (Genbank Accession No. AX092328);

(25) PSCA (Genbank Accession No. AJ297436);

(26) GEDA (Genbank Accession No. AY260763);

(27) BAFF-R (B cell-activating factor receptor, BLyS receptor, BR3; NP_443177.1);

(28) CD22 (B-cell receptor CD22-B isoform; NP-001762.1);

(29) CD79a (CD79A, CD79α, immunoglobulin-associated alpha, a B cell-specific protein that covalently interacts with Ig beta (CD79B) and forms a complex on the surface with IgM molecules, transduces a signal involved in B-cell differentiation; Genbank Accession No. NP_001774.1);

(30) CXCR5 (Burkitt's lymphoma receptor 1, a G protein-coupled receptor that is activated by the CXCL 13 chemokine, functions in lymphocyte migration and humoral defense, plays a role in HIV-2 infection and regarded for development of AIDS, lymphoma, myeloma, and leukemia; Genbank Accession No. NP_001707.1);

(31) HLA-DOB (Beta subunit of MHC class II molecule (la antigen) that binds peptides and presents them to CD4+T lymphocytes; Genbank Accession No. NP_002111.1);

(32) P2X5 (Purinergic receptor P2X ligand-gated ion channel 5, an ion channel gated by extracellular ATP, may be involved in synaptic transmission and neurogenesis, and its deficiency may contribute to the pathophysiology of idiopathic detrusor instability; Genbank Accession No. NP_002552.2);

(33) CD72 (B-cell differentiation antigen CD72, Lyb-2; Genbank Accession No. NP_001773.1);

(34) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis; Genbank Accession No. NP_005573.1);

(35) FcRH1 (Fc receptor-like protein 1, a putative receptor for the immunoglobulin Fc domain that contains C2 type Ig-like and ITAM domains, may have a role in B-lymphocyte differentiation; Genbank Accession No. NP_443170.1);

(36) IRTA2 (Immunoglobulin superfamily receptor translocation associated 2, a putative immunoreceptor with possible roles in B cell development and lymphomagenesis; deregulation of the gene by translocation occurs in some B cell malignancies; Genbank Accession No. NP_112571.1);

(37) TENB2 (putative transmembrane proteoglycan, related to the EGF/hereulin family of growth factors and follistatin; Genbank Accession No. AF179274);

(38) MAGE-C1/CT7 (protein overexpressed in testicular cancer);

(39) androgen receptor, PTEN, human kallikrein-related peptidase 3 (protein overexpressed in prostate cancer);

(40) CD20;
(41) CD30;
(42) CD33;
(43) CD52;
(44) EpCam;
(45) CEA;
(46) gpA33;
(47) Mucins;
(48) TAG-72;
(49) Carbonic anhydrase IX;
(50) PSMA;
(51) folate receptor (protein family overexpressed by FOLR gene having a binding affinity for folic acid, and intracellularly delivering 5-methyltetrahydrofolate);
(52) gangliosides (GD2, GD3, GM2);
(53) hydrate/saccharide Lewis-Y;
(54) VEGF;
(55) VEGFR;
(56) aVb3;
(57) a5b1;
(58) ERB3;
(59) c-MET;
(60) EphA3;
(61) TRAIL-R1, TRAIL-R2;
(62) RANKL;
(63) FAP; and
(64) Tenascin.

9. The antibody-drug conjugate of claim 1, wherein the antibody comprises either the variable region and the CH1, CH2 and CH3 of IgG2 or IgG4, or the Fab (of the modified antibody) and the Fc of IgG2 or IgG4.

10. The antibody-drug conjugate of claim 1, wherein the drug is conjugated to the cysteine residue or X in the motif.

11. A method of treating cancer, which comprises the antibody-drug conjugate of claim 1 as an active ingredient, wherein the antibody is specific for an antigen of said cancer, and wherein the drug of the antibody-drug conjugate comprises an anticancer drug for said cancer.

* * * * *

UNITED STATES PATENT AND TRADEMARK OFFICE
CERTIFICATE OF CORRECTION

Page 1 of 1

PATENT NO. : 12,090,210 B2
APPLICATION NO. : 17/551103
DATED : September 17, 2024
INVENTOR(S) : Soon Jae Park et al.

It is certified that error appears in the above-identified patent and that said Letters Patent is hereby corrected as shown below:

In the Specification

Column 1, Line 23, "440 DIV_SeqListing_ST25.txt" should be -- "440DIV_SeqListing_ST25.txt" --.

Column 4, Line 65, "to 20" should be -- 0 to 20 --.

Column 6, Line 35, "ACGHA" should be -- AXGHA --.

Column 6, Line 39, "to 20" should be -- 0 to 20 --.

Column 19, Line 30, "CHO-KI" should be -- CHO-K1 --.

Column 19, Lines 41-42, "MW-25,000" should be -- MW~25,000 --.

In the Claims

Column 95, Line 9, Claim 8 "C530008016Rik" should be -- C530008O16Rik --.

Column 97, Line 7, Claim 11 "anticancer" should be -- anti-cancer --.

Signed and Sealed this
Thirteenth Day of May, 2025

Coke Morgan Stewart
*Acting Director of the United States Patent and Trademark Office*

SEQUENCE LISTING

```
<160> NUMBER OF SEQ ID NOS: 128

<210> SEQ ID NO 1
<211> LENGTH: 5
<212> TYPE: PRT
<213> ORGANISM: Artificial Sequence
<220> FEATURE:
<223> OTHER INFORMATION: Motif

<400> SEQUENCE: 1

Ala Cys Gly His Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Motif

<400> SEQUENCE: 2

Ala His Gly Cys Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa is any amino acid residue

<400> SEQUENCE: 3

Ala Xaa Gly His Ala
1               5

<210> SEQ ID NO 4
<211> LENGTH: 5
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (4)..(4)
<223> OTHER INFORMATION: Xaa is any amino acid residue

<400> SEQUENCE: 4

Ala His Gly Xaa Ala
1               5

<210> SEQ ID NO 5
<211> LENGTH: 10
<212> TYPE: PRT
<213> ORGANISM: Artificial Sequence
<220> FEATURE:
<223> OTHER INFORMATION: Motif

<400> SEQUENCE: 5

Ala Cys Gly His Ala Ala Cys Gly His Ala
1               5                   10

<210> SEQ ID NO 6
<211> LENGTH: 10
<212> TYPE: PRT
```

```
<213> ORGANISM: Artificial Sequence
<220> FEATURE:
<223> OTHER INFORMATION: Motif

<400> SEQUENCE: 6

Ala Cys Gly His Ala Ala His Gly Cys Ala
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (7)..(7)
<223> OTHER INFORMATION: Xaa is any amino acid residue

<400> SEQUENCE: 7

Ala Cys Gly His Ala Ala Xaa Gly His Ala
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (9)..(9)
<223> OTHER INFORMATION: Xaa is any amino acid residue

<400> SEQUENCE: 8

Ala Cys Gly His Ala Ala His Gly Xaa Ala
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Motif

<400> SEQUENCE: 9

Ala His Gly Cys Ala Ala His Gly Cys Ala
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Motif

<400> SEQUENCE: 10

Ala His Gly Cys Ala Ala Cys Gly His Ala
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (7)..(7)
```

<223> OTHER INFORMATION: Xaa is any amino acid residue

<400> SEQUENCE: 11

Ala His Gly Cys Ala Ala Xaa Gly His Ala
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (9)..(9)
<223> OTHER INFORMATION: Xaa is any amino acid residue

<400> SEQUENCE: 12

Ala His Gly Cys Ala Ala His Gly Xaa Ala
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa is any amino acid residue
<220> FEATURE:
<221> NAME/KEY: MISC_FEATURE
<222> LOCATION: (7)..(7)
<223> OTHER INFORMATION: Xaa is any amino acid residue

<400> SEQUENCE: 13

Ala Xaa Gly His Ala Ala Xaa Gly His Ala
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa is any amino acid residue

<400> SEQUENCE: 14

Ala Xaa Gly His Ala Ala Cys Gly His Ala
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa is any amino acid residue

<400> SEQUENCE: 15

Ala Xaa Gly His Ala Ala His Gly Cys Ala
1               5                   10

```
<210> SEQ ID NO 16
<211> LENGTH: 10
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa is any amino acid residue
<220> FEATURE:
<221> NAME/KEY: MISC_FEATURE
<222> LOCATION: (9)..(9)
<223> OTHER INFORMATION: Xaa is any amino acid residue

<400> SEQUENCE: 16

Ala Xaa Gly His Ala Ala His Gly Xaa Ala
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (4)..(4)
<223> OTHER INFORMATION: Xaa is any amino acid residue
<220> FEATURE:
<221> NAME/KEY: MISC_FEATURE
<222> LOCATION: (9)..(9)
<223> OTHER INFORMATION: Xaa is any amino acid residue

<400> SEQUENCE: 17

Ala His Gly Xaa Ala Ala His Gly Xaa Ala
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (4)..(4)
<223> OTHER INFORMATION: Xaa is any amino acid residue

<400> SEQUENCE: 18

Ala His Gly Xaa Ala Ala Cys Gly His Ala
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (4)..(4)
<223> OTHER INFORMATION: Xaa is any amino acid residue

<400> SEQUENCE: 19

Ala His Gly Xaa Ala Ala His Gly Cys Ala
1               5                   10

<210> SEQ ID NO 20
<211> LENGTH: 10
```

```
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (4)..(4)
<223> OTHER INFORMATION: Xaa is any amino acid residue
<220> FEATURE:
<221> NAME/KEY: MISC_FEATURE
<222> LOCATION: (7)..(7)
<223> OTHER INFORMATION: Xaa is any amino acid residue

<400> SEQUENCE: 20

Ala His Gly Xaa Ala Ala Xaa Gly His Ala
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Motif

<400> SEQUENCE: 21

Ala Cys Gly His Ala Ala Ser Gly His Ala
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Motif

<400> SEQUENCE: 22

Ala Cys Gly His Ala Ala His Gly Ser Ala
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Motif

<400> SEQUENCE: 23

Ala His Gly Cys Ala Ala Ser Gly His Ala
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Motif

<400> SEQUENCE: 24

Ala His Gly Cys Ala Ala His Gly Ser Ala
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Motif
```

```
<400> SEQUENCE: 25

Ala Ser Gly His Ala Ala Ser Gly His Ala
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Motif

<400> SEQUENCE: 26

Ala Ser Gly His Ala Ala Cys Gly His Ala
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Motif

<400> SEQUENCE: 27

Ala Ser Gly His Ala Ala His Gly Cys Ala
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Motif

<400> SEQUENCE: 28

Ala Ser Gly His Ala Ala His Gly Ser Ala
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Motif

<400> SEQUENCE: 29

Ala His Gly Ser Ala Ala His Gly Ser Ala
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Motif

<400> SEQUENCE: 30

Ala His Gly Ser Ala Ala Cys Gly His Ala
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Motif
```

```
<400> SEQUENCE: 31

Ala His Gly Ser Ala Ala His Gly Cys Ala
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Motif

<400> SEQUENCE: 32

Ala His Gly Ser Ala Ala Ser Gly His Ala
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Motif

<400> SEQUENCE: 33

Ala Cys Gly His Ala Ala Ala Gly His Ala
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Motif

<400> SEQUENCE: 34

Ala Cys Gly His Ala Ala His Gly Ala Ala
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Motif

<400> SEQUENCE: 35

Ala His Gly Cys Ala Ala Ala Gly His Ala
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Motif

<400> SEQUENCE: 36

Ala His Gly Cys Ala Ala His Gly Ala Ala
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Motif
```

<400> SEQUENCE: 37

Ala Ala Gly His Ala Ala Gly His Ala
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Motif

<400> SEQUENCE: 38

Ala Ala Gly His Ala Ala Cys Gly His Ala
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Motif

<400> SEQUENCE: 39

Ala Ala Gly His Ala Ala His Gly Cys Ala
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Motif

<400> SEQUENCE: 40

Ala Ala Gly His Ala Ala His Gly Ala Ala
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Motif

<400> SEQUENCE: 41

Ala His Gly Ala Ala Ala His Gly Ala Ala
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Motif

<400> SEQUENCE: 42

Ala His Gly Ala Ala Ala Cys Gly His Ala
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Motif

<400> SEQUENCE: 43

Ala His Gly Ala Ala Ala His Gly Cys Ala
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Motif

<400> SEQUENCE: 44

Ala His Gly Ala Ala Ala Ala Gly His Ala
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Motif

<400> SEQUENCE: 45

Ala Cys Gly His Ala Ala Thr Gly His Ala
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Motif

<400> SEQUENCE: 46

Ala Cys Gly His Ala Ala His Gly Thr Ala
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Motif

<400> SEQUENCE: 47

Ala His Gly Cys Ala Ala Thr Gly His Ala
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Motif

<400> SEQUENCE: 48

Ala His Gly Cys Ala Ala His Gly Thr Ala
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Motif

<400> SEQUENCE: 49

Ala Thr Gly His Ala Ala Thr Gly His Ala
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Motif

<400> SEQUENCE: 50

Ala Thr Gly His Ala Ala Cys Gly His Ala
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Motif

<400> SEQUENCE: 51

Ala Thr Gly His Ala Ala His Gly Cys Ala
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Motif

<400> SEQUENCE: 52

Ala Thr Gly His Ala Ala His Gly Thr Ala
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Motif

<400> SEQUENCE: 53

Ala His Gly Thr Ala Ala His Gly Thr Ala
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Motif

<400> SEQUENCE: 54

Ala His Gly Thr Ala Ala Cys Gly His Ala
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Motif

```
<400> SEQUENCE: 55

Ala His Gly Thr Ala Ala His Gly Cys Ala
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Motif

<400> SEQUENCE: 56

Ala His Gly Thr Ala Ala Thr Gly His Ala
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Motif

<400> SEQUENCE: 57

Ala Cys Gly His Ala Ala Tyr Gly His Ala
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Motif

<400> SEQUENCE: 58

Ala Cys Gly His Ala Ala His Gly Tyr Ala
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Motif

<400> SEQUENCE: 59

Ala His Gly Cys Ala Ala Tyr Gly His Ala
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Motif

<400> SEQUENCE: 60

Ala His Gly Cys Ala Ala His Gly Tyr Ala
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Motif
```

```
<400> SEQUENCE: 61

Ala Tyr Gly His Ala Ala Tyr Gly His Ala
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Motif

<400> SEQUENCE: 62

Ala Tyr Gly His Ala Ala Cys Gly His Ala
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Motif

<400> SEQUENCE: 63

Ala Tyr Gly His Ala Ala His Gly Cys Ala
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Motif

<400> SEQUENCE: 64

Ala Tyr Gly His Ala Ala His Gly Tyr Ala
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Motif

<400> SEQUENCE: 65

Ala His Gly Tyr Ala Ala His Gly Tyr Ala
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Motif

<400> SEQUENCE: 66

Ala His Gly Tyr Ala Ala Cys Gly His Ala
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Motif
```

```
<400> SEQUENCE: 67

Ala His Gly Tyr Ala Ala His Gly Cys Ala
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Motif

<400> SEQUENCE: 68

Ala His Gly Tyr Ala Ala Tyr Gly His Ala
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Motif

<400> SEQUENCE: 69

Ala Cys Gly His Ala Ala Asp Gly His Ala
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Motif

<400> SEQUENCE: 70

Ala Cys Gly His Ala Ala His Gly Asp Ala
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Motif

<400> SEQUENCE: 71

Ala His Gly Cys Ala Ala Asp Gly His Ala
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Motif

<400> SEQUENCE: 72

Ala His Gly Cys Ala Ala His Gly Asp Ala
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Motif
```

<400> SEQUENCE: 73

Ala Asp Gly His Ala Ala Asp Gly His Ala
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Motif

<400> SEQUENCE: 74

Ala Asp Gly His Ala Ala Cys Gly His Ala
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Motif

<400> SEQUENCE: 75

Ala Asp Gly His Ala Ala His Gly Cys Ala
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Motif

<400> SEQUENCE: 76

Ala Asp Gly His Ala Ala His Gly Asp Ala
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Motif

<400> SEQUENCE: 77

Ala His Gly Asp Ala Ala His Gly Asp Ala
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Motif

<400> SEQUENCE: 78

Ala His Gly Asp Ala Ala Cys Gly His Ala
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Motif

```
<400> SEQUENCE: 79

Ala His Gly Asp Ala Ala His Gly Cys Ala
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Motif

<400> SEQUENCE: 80

Ala His Gly Asp Ala Ala Asp Gly His Ala
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Motif

<400> SEQUENCE: 81

Ala Cys Gly His Ala Ala Lys Gly His Ala
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Motif

<400> SEQUENCE: 82

Ala Cys Gly His Ala Ala His Gly Lys Ala
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Motif

<400> SEQUENCE: 83

Ala His Gly Cys Ala Ala Lys Gly His Ala
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Motif

<400> SEQUENCE: 84

Ala His Gly Cys Ala Ala His Gly Lys Ala
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Motif
```

```
<400> SEQUENCE: 85

Ala Lys Gly His Ala Ala Lys Gly His Ala
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Motif

<400> SEQUENCE: 86

Ala Lys Gly His Ala Ala Cys Gly His Ala
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Motif

<400> SEQUENCE: 87

Ala Lys Gly His Ala Ala His Gly Cys Ala
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Motif

<400> SEQUENCE: 88

Ala Lys Gly His Ala Ala His Gly Lys Ala
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Motif

<400> SEQUENCE: 89

Ala His Gly Lys Ala Ala His Gly Lys Ala
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Motif

<400> SEQUENCE: 90

Ala His Gly Lys Ala Ala Cys Gly His Ala
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Motif
```

```
<400> SEQUENCE: 91

Ala His Gly Lys Ala Ala His Gly Lys Ala
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Motif

<400> SEQUENCE: 92

Ala His Gly Lys Ala Ala Lys Gly His Ala
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Motif

<400> SEQUENCE: 93

Ala Cys Gly His Ala Ala Phe Gly His Ala
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Motif

<400> SEQUENCE: 94

Ala Cys Gly His Ala Ala His Gly Phe Ala
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Motif

<400> SEQUENCE: 95

Ala His Gly Cys Ala Ala Phe Gly His Ala
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Motif

<400> SEQUENCE: 96

Ala His Gly Cys Ala Ala His Gly Phe Ala
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Motif
```

<400> SEQUENCE: 97

Ala Phe Gly His Ala Ala Phe Gly His Ala
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Motif

<400> SEQUENCE: 98

Ala Phe Gly His Ala Ala Cys Gly His Ala
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Motif

<400> SEQUENCE: 99

Ala Phe Gly His Ala Ala His Gly Cys Ala
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Motif

<400> SEQUENCE: 100

Ala Phe Gly His Ala Ala His Gly Phe Ala
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Motif

<400> SEQUENCE: 101

Ala His Gly Phe Ala Ala His Gly Phe Ala
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Motif

<400> SEQUENCE: 102

Ala His Gly Phe Ala Ala Cys Gly His Ala
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Motif

<400> SEQUENCE: 103

Ala His Gly Phe Ala Ala His Gly Phe Ala
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Motif

<400> SEQUENCE: 104

Ala His Gly Phe Ala Ala Phe Gly His Ala
1               5                   10

<210> SEQ ID NO 105
<211> LENGTH: 38
<212> TYPE: DNA
<213> ORGANISM: Artificial Sequence
<220> FEATURE:
<223> OTHER INFORMATION: Primer

<400> SEQUENCE: 105
gctcctcgag gccaccatgg gatggagctg tatcatcc                           38

<210> SEQ ID NO 106
<211> LENGTH: 69
<212> TYPE: DNA
<213> ORGANISM: Artificial Sequence
<220> FEATURE:
<223> OTHER INFORMATION: Primer

<400> SEQUENCE: 106
ccatgcggcc gctcatttag gcatggccac aagcagcatg ccacaggca cccggagaca    60 gggagaggc                                                           69

<210> SEQ ID NO 107
<211> LENGTH: 38
<212> TYPE: DNA
<213> ORGANISM: Artificial Sequence
<220> FEATURE:
<223> OTHER INFORMATION: Primer

<400> SEQUENCE: 107
gctcctcgag gccaccatgg gatggagctg tatcatcc                           38

<210> SEQ ID NO 108
<211> LENGTH: 60
<212> TYPE: DNA
<213> ORGANISM: Artificial Sequence
<220> FEATURE:
<223> OTHER INFORMATION: Primer

<400> SEQUENCE: 108
ccatgcggcc gctcatttag gcatggccac aagcacctcc accaccgga cagggaga     60

<210> SEQ ID NO 109
<211> LENGTH: 38
<212> TYPE: DNA
<213> ORGANISM: Artificial Sequence
<220> FEATURE:
<223> OTHER INFORMATION: Primer

<400> SEQUENCE: 109
gctcctcgag gccaccatgg gatggagctg tatcatcc                           38

-continued

<210> SEQ ID NO 110
<211> LENGTH: 78
<212> TYPE: DNA
<213> ORGANISM: Artificial Sequence
<220> FEATURE:
<223> OTHER INFORMATION: Primer

<400> SEQUENCE: 110
ccatgcggcc gctcatttag gcatggccac aagcacctcc accagcatgg ccacaggcac    60
ccggagacag ggagaggc                                                  78

<210> SEQ ID NO 111
<211> LENGTH: 38
<212> TYPE: DNA
<213> ORGANISM: Artificial Sequence
<220> FEATURE:
<223> OTHER INFORMATION: Primer

<400> SEQUENCE: 111
gctcctcgag gccaccatgg gatggagctg tatcatcc                            38

<210> SEQ ID NO 112
<211> LENGTH: 63
<212> TYPE: DNA
<213> ORGANISM: Artificial Sequence
<220> FEATURE:
<223> OTHER INFORMATION: Primer

<400> SEQUENCE: 112
cagattgcgg ccgctcatta ggcatggcca caagcagcat ggcctgaggc acccggagac    60
agg                                                                  63

<210> SEQ ID NO 113
<211> LENGTH: 38
<212> TYPE: DNA
<213> ORGANISM: Artificial Sequence
<220> FEATURE:
<223> OTHER INFORMATION: Primer

<400> SEQUENCE: 113
gctcctcgag gccaccatgg gatggagctg tatcatcc                            38

<210> SEQ ID NO 114
<211> LENGTH: 63
<212> TYPE: DNA
<213> ORGANISM: Artificial Sequence
<220> FEATURE:
<223> OTHER INFORMATION: Primer

<400> SEQUENCE: 114
cagattgcgg ccgctcatta ggcatggcct gaagcagcat ggccacaggc acccggagac    60
agg                                                                  63

<210> SEQ ID NO 115
<211> LENGTH: 448
<212> TYPE: PRT
<213> ORGANISM: Artificial Sequence
<220> FEATURE:
<223> OTHER INFORMATION: Heavy Chain of Fwt

<400> SEQUENCE: 115

Glu Val Gln Leu Val Glu Ser Gly Gly Gly Val Val Gln Pro Gly Arg
1               5                   10                  15

```
Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

Ala Leu His Asn His Tyr Thr Gln Lys Ser Leu Ser Leu Ser Pro Gly
            435                 440                 445

<210> SEQ ID NO 116
<211> LENGTH: 217
<212> TYPE: PRT
<213> ORGANISM: Artificial Sequence
<220> FEATURE:
<223> OTHER INFORMATION: Light Chain of Fwt

<400> SEQUENCE: 116

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ile Ser Ser Asn
            20                  25                  30

Asn Leu His Trp Tyr Gln Gln Lys Pro Gly Lys Ala Pro Lys Pro Trp
            35                  40                  45

Ile Tyr Gly Thr Ser Asn Leu Ala Ser Gly Val Pro Ser Arg Phe Ser
50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 117
<211> LENGTH: 458
<212> TYPE: PRT
<213> ORGANISM: Artificial Sequence
<220> FEATURE:
<223> OTHER INFORMATION: FM2 Heavy Chain

<400> SEQUENCE: 117

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
            35                  40                  45

Ala Met Ile Ser Ser Gly Gly Ser Tyr Thr Tyr Tyr Ala Asp Ser Val
50                  55                  60

Lys Gly Arg Phe Ala Ile Ser Arg Asp Asn Ala Lys Asn Thr Leu Phe
65                  70                  75                  80

```
Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Cys Gly His Ala Ala Cys Gly His Ala
    450                 455

<210> SEQ ID NO 118
<211> LENGTH: 458
<212> TYPE: PRT
<213> ORGANISM: Artificial Sequence
<220> FEATURE:
```

<223> OTHER INFORMATION: FM2a Heavy Chain

<400> SEQUENCE: 118

```
Glu Val Gln Leu Val Glu Ser Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
            35                  40                  45

Ala Met Ile Ser Ser Gly Gly Ser Tyr Thr Tyr Tyr Ala Asp Ser Val
        50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Ala Ser Gly His Ala Ala Cys Gly His Ala
            450                 455

<210> SEQ ID NO 119
<211> LENGTH: 458
<212> TYPE: PRT
<213> ORGANISM: Artificial Sequence
<220> FEATURE:
<223> OTHER INFORMATION: FM2b Heavy Chain

<400> SEQUENCE: 119

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Ala Cys Gly His Ala Ala Ser Gly His Ala
    450                 455

<210> SEQ ID NO 120
<211> LENGTH: 456
<212> TYPE: PRT
<213> ORGANISM: Artificial Sequence
<220> FEATURE:
<223> OTHER INFORMATION: FM1 Heavy Chain

<400> SEQUENCE: 120

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
                20                  25                  30

Gly Leu Ser Trp Val Arg Gln Ala Pro Gly Lys Gly Leu Glu Trp Val
            35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Ala Cys Gly His Ala
        450                 455

<210> SEQ ID NO 121
<211> LENGTH: 461
<212> TYPE: PRT
<213> ORGANISM: Artificial Sequence
<220> FEATURE:
<223> OTHER INFORMATION: FM2L Heavy Chain

<400> SEQUENCE: 121

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

```
Thr Pro Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Cys Gly His Ala Gly Gly Ala Cys Gly His Ala
450                 455                 460

<210> SEQ ID NO 122
<211> LENGTH: 131
<212> TYPE: PRT
<213> ORGANISM: Artificial Sequence
<220> FEATURE:
<223> OTHER INFORMATION: Fwt Hv

<400> SEQUENCE: 122

Glu Val Gln Leu Val Glu Ser Gly Gly Gly Val Val Gln Pro Gly Arg
1               5                   10                  15
```

```
Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
            35                  40                  45

Ala Met Ile Ser Ser Gly Gly Ser Tyr Thr Tyr Tyr Ala Asp Ser Val
 50                  55                  60

Lys Gly Arg Phe Ala Ile Ser Arg Asp Asn Ala Lys Asn Thr Leu Phe
 65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser Ala Ser Thr Lys Gly Pro Ser Val Phe
            115                 120                 125

Pro Leu Ala
    130
```

<210> SEQ ID NO 123
<211> LENGTH: 113
<212> TYPE: PRT
<213> ORGANISM: Artificial Sequence
<220> FEATURE:
<223> OTHER INFORMATION: Fwt Lv

<400> SEQUENCE: 123

```
Asp Ile Gln Leu Thr Gln Ser Pro Ser Ser Leu Ser Ala Ser Val Gly
 1               5                  10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
            35                  40                  45

Ile Tyr Gly Thr Ser Asn Leu Ala Ser Gly Val Pro Ser Arg Phe Ser
 50                  55                  60

Gly Ser Gly Ser Gly Thr Asp Tyr Thr Phe Thr Ile Ser Ser Leu Gln
 65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys Arg Thr
            100                 105                 110

Val
```

<210> SEQ ID NO 124
<211> LENGTH: 227
<212> TYPE: PRT
<213> ORGANISM: Artificial Sequence
<220> FEATURE:
<223> OTHER INFORMATION: Fwt Fab

<400> SEQUENCE: 124

```
Glu Val Gln Leu Val Glu Ser Gly Gly Gly Val Val Gln Pro Gly Arg
 1               5                  10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
            35                  40                  45

Ala Met Ile Ser Ser Gly Gly Ser Tyr Thr Tyr Tyr Ala Asp Ser Val
 50                  55                  60
```

```
Lys Gly Arg Phe Ala Ile Ser Arg Asp Asn Ala Lys Asn Thr Leu Phe
 65                  70                  75                  80

Leu Gln Met Asp Ser Leu Arg Pro Glu Asp Thr Gly Val Tyr Phe Cys
                 85                  90                  95

Ala Arg His Gly Asp Asp Pro Ala Trp Phe Ala Tyr Trp Gly Gln Gly
            100                 105                 110

Thr Pro Val Thr Val Ser Ser Ala Ser Thr Lys Gly Pro Ser Val Phe
            115                 120                 125

Pro Leu Ala Pro Ser Ser Lys Ser Thr Ser Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr
225

<210> SEQ ID NO 125
<211> LENGTH: 1350
<212> TYPE: DNA
<213> ORGANISM: Artificial Sequence
<220> FEATURE:
<223> OTHER INFORMATION: Fwt Heavy Chain

<400> SEQUENCE: 125
gaggtccaac tggtggagag cggtggaggt gttgtgcaac tggccggtc cctgcgcctg      60 tcctgctccg catctggctt caccttcagc ggctatgggt tgtcttgggt gagacaggca     120
cctggaaaag gtcttgagtg ggttgcaatg attagtagtg gtggtagtta tacctactat     180
gcagacagtg tgaagggtag atttgcaata tcgcgagaca cgccaagaa cacattgttc      240 ctgcaaatgg acagcctgag acccgaagac accggggtct attttttgtgc aagacatggg   300 gacgatcccg cctggttcgc ttattgggc caagggaccc cggtcaccgt ctcctcagcc     360
tccaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggatgagctg   1080
```
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc cgggaaatga                                     1350

<210> SEQ ID NO 126
<211> LENGTH: 654
<212> TYPE: DNA
<213> ORGANISM: Artificial Sequence
<220> FEATURE:
<223> OTHER INFORMATION: Fwt Light Chain

<400> SEQUENCE: 126
gacatccagc tgacccagag cccaagcagc ctgagcgcca gcgtgggtga cagagtgacc      60
atcacctgta gtgtcagctc aagtataagt tccaacaact tgcactggta ccagcagaag    120
ccaggtaagg ctccaaagcc atggatctac ggcacatcca acctggcttc tggtgtgcca    180
agcagattca gcggtagcgg tagcggtacc gactacacct tcaccatcag cagcctccag    240
ccagaggaca tcgccaccta ctactgccaa cagtggagta gttacccgta catgtacacg    300
ttcggccaag ggaccaaggt ggaaatcaaa cgaactgtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgcccc tcaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg ttaa           654

<210> SEQ ID NO 127
<211> LENGTH: 451
<212> TYPE: PRT
<213> ORGANISM: Artificial Sequence
<220> FEATURE:
<223> OTHER INFORMATION: Trastuzumab Heavy chain

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 128
<211> LENGTH: 214
<212> TYPE: PRT
<213> ORGANISM: Artificial Sequence
<220> FEATURE:
<223> OTHER INFORMATION: Trastuzumab Light chain

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

```
Tyr Ser Ala Ser Phe Leu Tyr Ser Gly Val Pro Ser Arg Phe Ser Gly
    50              55              60

Ser Arg Ser Gly Thr Asp Phe Thr Leu Thr Ile Ser Ser Leu Gln Pro
65              70              75              80

Glu Asp Phe Ala Thr Tyr Tyr Cys Gln Gln His Tyr Thr Thr Pro Pro
                85              90              95

Thr Phe Gly Gln Gly Thr Lys Val Glu Ile Lys Arg Thr Val Ala Ala
                100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
                165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
            195             200             205

Phe Asn Arg Gly Glu Cys
210
```